United States Patent
Rahman et al.

(10) Patent No.: US 9,576,359 B2
(45) Date of Patent: Feb. 21, 2017

(54) CONTEXT BASED ALGORITHMIC FRAMEWORK FOR IDENTIFYING AND CLASSIFYING EMBEDDED IMAGES OF FOLLICLE UNITS

(71) Applicants: The Florida International University Board of Trustees, Miami, FL (US); NRG Medical, LLC, Coral Gables, FL (US)

(72) Inventors: Md Mahbubur Rahman, Miami, FL (US); S. S. Iyengar, Miami, FL (US); Wei Zeng, Miami, FL (US); Frank Hernandez, Miami, FL (US); Bernard Nusbaum, Coral Gables, FL (US); Paul Rose, Coral Gables, FL (US)

(73) Assignees: The Florida International University Board of Trustees, Miami, FL (US); NRG Medical, LLC, Coral Gables, FL (US)

( * ) Notice: Subject to any disclaimer, the term of this patent is extended or adjusted under 35 U.S.C. 154(b) by 0 days.

(21) Appl. No.: 15/033,778

(22) PCT Filed: Nov. 3, 2014

(86) PCT No.: PCT/US2014/063699
§ 371 (c)(1),
(2) Date: May 2, 2016

(87) PCT Pub. No.: WO2015/066618
PCT Pub. Date: May 7, 2015

(65) Prior Publication Data
US 2016/0253799 A1 Sep. 1, 2016

Related U.S. Application Data

(60) Provisional application No. 61/898,836, filed on Nov. 1, 2013.

(51) Int. Cl.
*G06K 9/00* (2006.01)
*G06T 7/00* (2006.01)
(Continued)

(52) U.S. Cl.
CPC ......... *G06T 7/0012* (2013.01); *G06F 19/3481* (2013.01); *G06K 9/4638* (2013.01);
(Continued)

(58) Field of Classification Search
CPC ................... G06T 7/0042; G06T 2207/30004; G06T 2207/30088; G06T 7/0081; G06T 7/0083
See application file for complete search history.

(56) References Cited

U.S. PATENT DOCUMENTS 6,389,150 B1 * 5/2002 Amornsiripanitch ... A61B 5/1072
382/100
6,956,587 B1 10/2005 Anson
(Continued)

FOREIGN PATENT DOCUMENTS

JP 2001-141838 A 5/2001
JP 2001141838 A * 5/2001
(Continued)

OTHER PUBLICATIONS

Hofmann, Rolf. "TrichoScan: A Novel Tool for the Analysis of Hair Growth In Vivo," Journal of Investigative Dermatology Symposium Proceedings, Jun. 2003, 8(1):109-115.
(Continued)

*Primary Examiner* — Stephen R Koziol
*Assistant Examiner* — Jonathan S Lee
(74) *Attorney, Agent, or Firm* — Saliwanchik, Lloyd & Eisenschenk

(57) ABSTRACT

The subject invention provides a method for detecting and analyzing the hair follicles on a scalp to assist with hair
(Continued)

follicle transplantation. The methods of the subject invention are able to count the number of hair follicle groups and the number of follicles within each group based upon a microscopic image of a sample from a human scalp. An algorithm is then used to cluster the follicles and generate a neighboring connected graph to calculate the inter object distances. A report can then be generated that provides information regarding the density, placement, and percentage of hair follicle type in different areas of the scalp. This report can be used to generate a hair follicle transplant strategy to assist a physician or robotic system.

20 Claims, 35 Drawing Sheets

(51) Int. Cl.
| | |
|---|---|
| *G06T 7/60* | (2006.01) |
| *G06F 19/00* | (2011.01) |
| *G06K 9/46* | (2006.01) |
| *G06K 9/62* | (2006.01) |
| *G06T 3/60* | (2006.01) |
| *G06T 5/00* | (2006.01) |

(52) U.S. Cl.
CPC ......... *G06K 9/4652* (2013.01); *G06K 9/6218* (2013.01); *G06T 3/60* (2013.01); *G06T 5/002* (2013.01); *G06T 7/60* (2013.01); *G06T 2207/10024* (2013.01); *G06T 2207/10056* (2013.01); *G06T 2207/20104* (2013.01); *G06T 2207/20132* (2013.01); *G06T 2207/30088* (2013.01); *G06T 2207/30204* (2013.01)

(56) References Cited

U.S. PATENT DOCUMENTS

| | | | |
|---|---|---|---|
| 8,290,229 B2 | 10/2012 | Qureshi et al. | |
| 2007/0106307 A1* | 5/2007 | Bodduluri | A61B 5/1077 606/133 |
| 2008/0049992 A1 | 2/2008 | Qureshi et al. | |
| 2008/0049993 A1* | 2/2008 | Qureshi | G06K 9/00 382/128 |
| 2010/0080415 A1* | 4/2010 | Qureshi | G06T 7/2033 382/103 |
| 2011/0022371 A1* | 1/2011 | Bodduluri | G06F 19/3437 703/11 |
| 2011/0251483 A1* | 10/2011 | Razzaque | A61B 6/466 600/424 |
| 2012/0158019 A1* | 6/2012 | Tenney | A61B 19/2203 606/133 |
| 2012/0215231 A1* | 8/2012 | Wesley | A61B 1/00087 606/133 |
| 2013/0058543 A1* | 3/2013 | Thomas | A45D 44/005 382/118 |
| 2014/0031691 A1* | 1/2014 | Nagase | A61B 8/466 600/443 |
| 2014/0261467 A1* | 9/2014 | Zhang | A61F 2/10 128/898 |
| 2014/0370070 A1* | 12/2014 | Lindner | A61L 27/3604 424/423 |

FOREIGN PATENT DOCUMENTS

| | | |
|---|---|---|
| KR | 10-2004-0089426 A | 10/2004 |
| KR | 20100103098 A | 9/2010 |
| KR | 20-2011-0003005 | 3/2011 |

OTHER PUBLICATIONS

International Search Report dated Jan. 27, 2015, for corresponding International Application No. PCT/US2014/063699.
Kalinke, Thomas etal., "A Texture-based Object Detection and an adaptive Model-based Classification," *IEEE International Conference on Intelligent Vehicles*, 1998, pp. 143-148.
Kumar, D. Girish et al., "A novel image processing technique for counting the number of trees in a satellite image," *European Journal of Applied Engineering and Scientific Research*, 2012, 1(4):151-159.
Lempitsky, Victor etal., "Learning to Count in Images," *NIPS*, 2010, pp. 1-9.

* cited by examiner

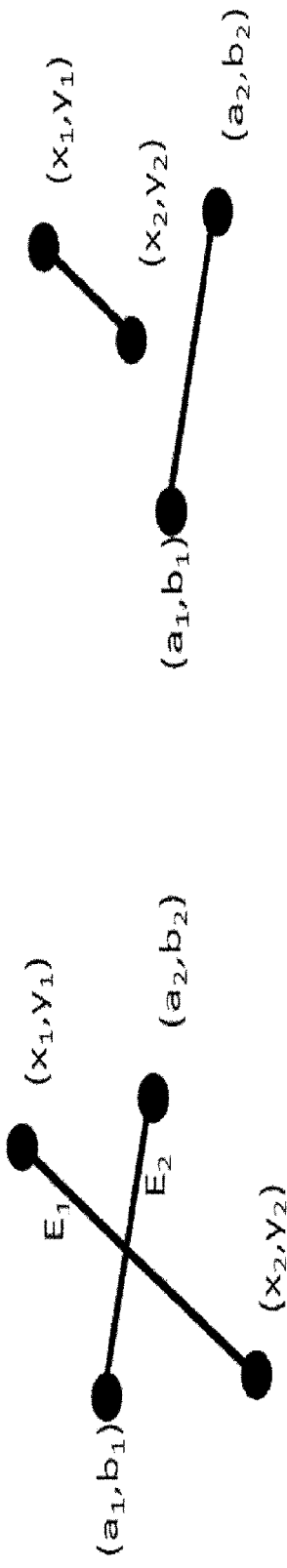
FIG. 10
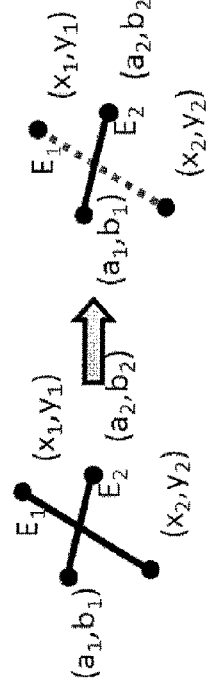
$length(E_1) > length(E_2)$. So E1 deleted
FIG. 11
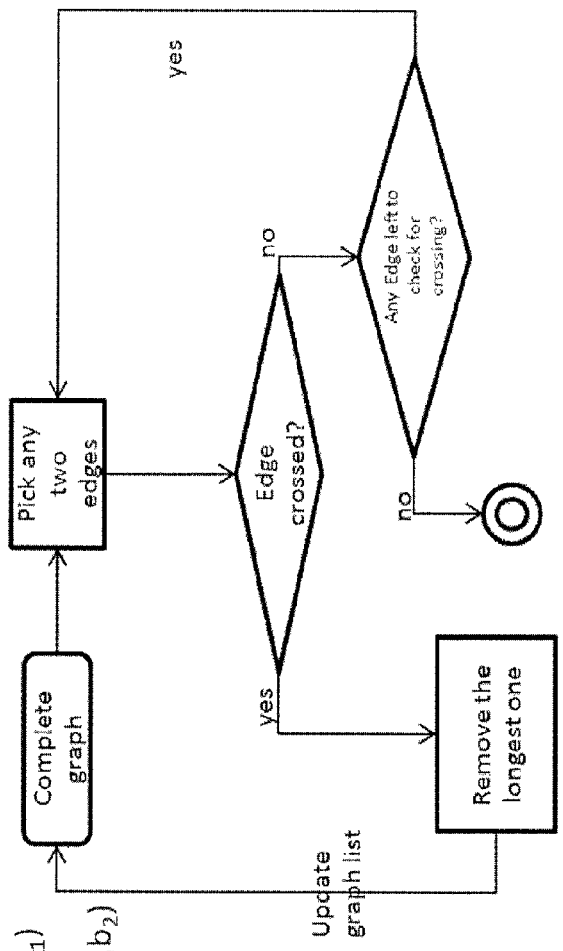
Flow Chart for Edge Crossing Removal

FIG. 16

| Image ID | Number of follicles in a group | Follicle Counting - Actual number of groups | Number of groups detected by our method | Accuracy |
|---|---|---|---|---|
| 3364A | 1 | 2 | 3 | 66.67% |
| | 2 | 3 | 4 | 75.00% |
| | 3 | 5 | 6 | 83.33% |
| | 4 | 6 | 3 | 50.00% |
| | 5 | 4 | 1 | 25.00% |
| 3364B | 1 | 3 | 4 | 75.00% |
| | 2 | 4 | 3 | 75.00% |
| | 3 | 6 | 6 | 100.00% |
| | 4 | 3 | 6 | 50.00% |
| | 5 | 1 | 1 | 100.00% |
| 3364C | 1 | 3 | 8 | 37.50% |
| | 2 | 4 | 5 | 80.00% |
| | 3 | 5 | 6 | 83.33% |
| | 4 | 4 | 4 | 100.00% |
| | 5 | 1 | 1 | 100.00% |
| 3364D | 1 | 4 | 2 | 50.00% |
| | 2 | 2 | 2 | 100.00% |
| | 3 | 5 | 3 | 60.00% |
| | 4 | 3 | 6 | 50.00% |
| | 5 | 1 | 1 | 100.00% |
| 37645A | 1 | 3 | 3 | 100.00% |
| | 2 | 11 | 9 | 81.82% |
| | 3 | 7 | 4 | 57.14% |
| | 4 | 4 | 8 | 50.00% |
| | 5 | 8 | 11 | 72.73% |
| | 6 | 2 | 2 | 100.00% |
| 37645B | 1 | 7 | 12 | 58.33% |
| | 2 | 12 | 10 | 83.33% |
| | 3 | 10 | 9 | 90.00% |
| | 4 | 4 | 4 | 100.00% |
| | 5 | 1 | 1 | 100.00% |

Problem Formulation

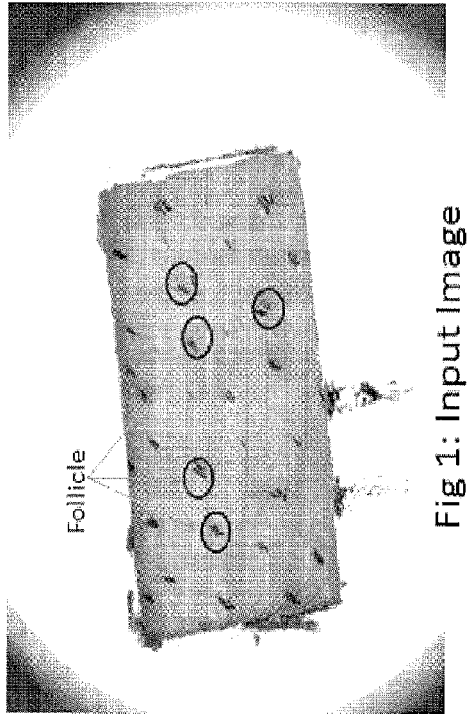

Fig 1: Input Image

FIG. 17B

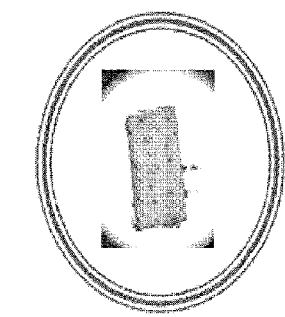

Problem Overview:

Our system begins with the image of Fig 1. The image needs to be sent to the server residing inside hybrid cloud by any of the http, ftp, tcp protocols. Another way is to use smartphones where the phones will act as client terminals.
Identify each follicle unit and know how many follicle units are there.
Cluster the follicle groups together and uniquely identify how many follicles are inside each cluster.
Know the inter-follicular distance among the follicle groups. We also need to measure the density of follicles on the bald surface.

Solution Sub Systems 100   FIG. 17C

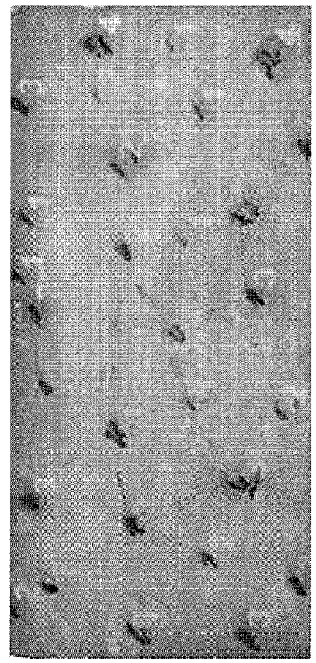

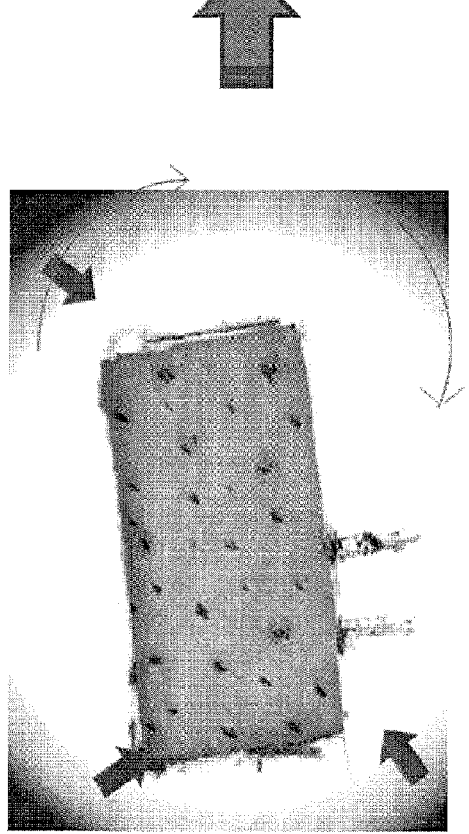

Result Image

We divided the solving steps into four sub systems

Feature Extraction Sub System: This system will extract the exact rectangular bald area from the image above. For this we need to detect the corners of the rectangular scalp area. Then we will identify the angle to be rotated to make this horizontal. Then we can crop the image to get the exact rectangular shaved scalp area.

Pre Processing Sub System: in this step we need to filter the background scalp area to separate the follicular units. This step needs noise filtration, smoothing, resizing and other standard image processing tasks.

Solution Sub Systems (contd.)

FIG. 17D

- Follicle Detection Sub System: This system needs to detect each follicle unit uniquely along with their 2D co-ordinate location in the image. The follicle units then need to feed into some clustering algorithm for grouping. After clustering we can get the number of follicles in each cluster and we will know the 2D co-ordinates of the clusters.
- Inter Follicular Distance Sub System: In this step we need to measure the interfollicular distances among the detected follicle clusters or groups. We need such a connected graph so that all the vertices (follicle group) will be connected only to respective neighbor vertices without any edge (inter follicular distance) crossings.

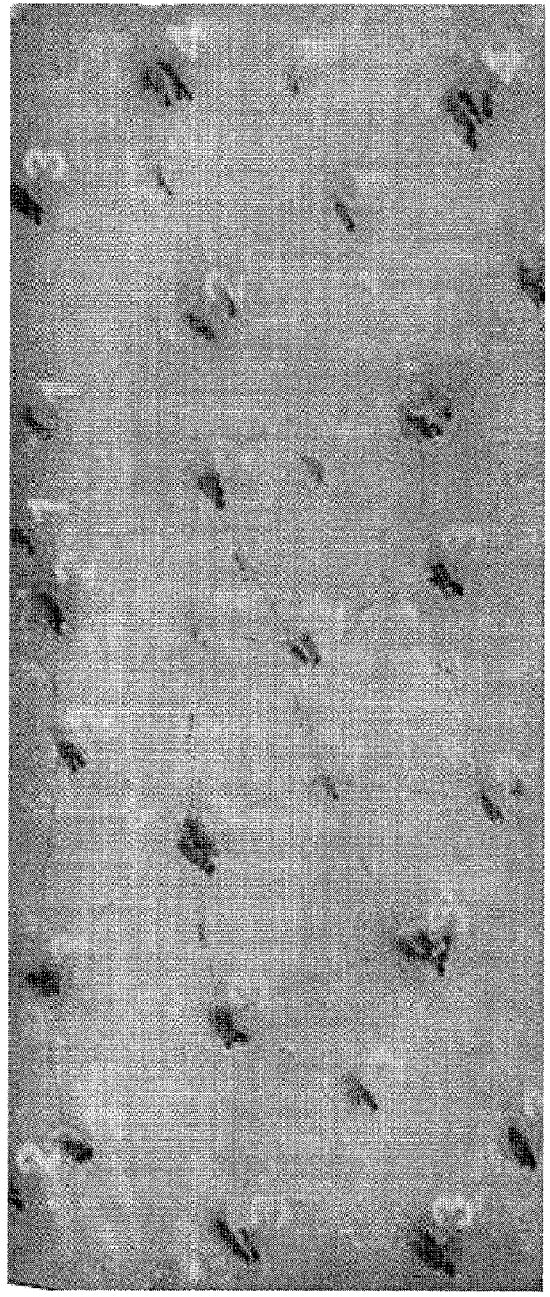

(1) Corner Detection

This mechanism assumes that there are elastic threads connecting the corners of the main image to the corners of the rectangular area. So the nearest dark region to each corner of the main image is the possible corner of the rectangular scalp. To make sure, once a possible corner is detected the technique then checks some surrounding pixels to determine whether it is a part of our ROI or a part of noise. If part of ROI then accept this as a corner, otherwise continue to search another nearest deep region to the corner. Threads always try to minimize its distance and eventually make the rectangular region horizontal.

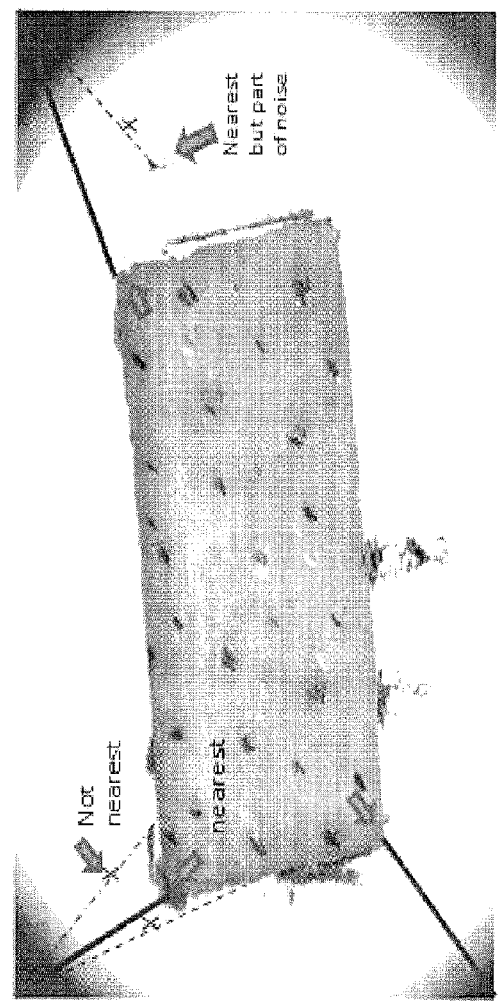

FIG. 17H

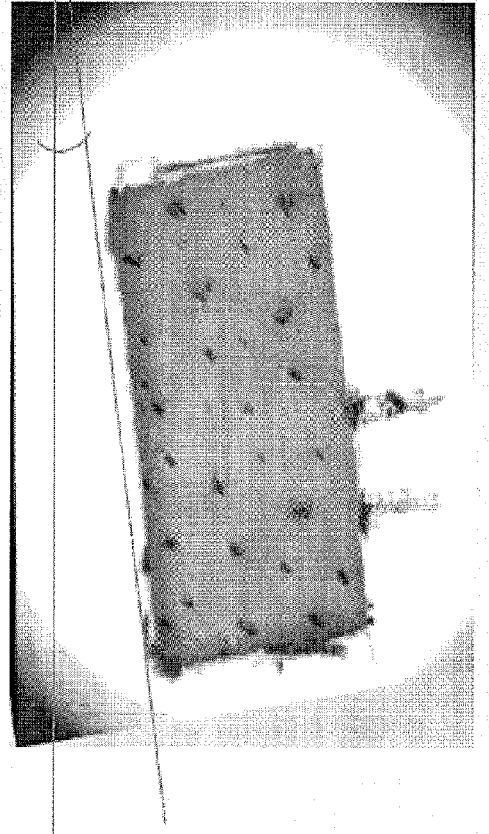

FIG. 17I (2) Angular Rotation

We need to rotate the image to make it horizontal. Because to crop an image with the existing API's we need to provide the start point, height and weight of the cropped area. Rotation angle can be found based on the equation. Then it is easy to rotate the image using Affine Transformation.

$$\theta = Arc\tan\left(\frac{upperlefty - upperrighty}{upperleftx - upperrightx}\right) \times \frac{180}{\pi}$$

After rotation the corner points are now relocated. We must find the new coordinates of the corners to crop the rectangular region from the image. From geometry we applied the following formulas:

$$upperleftX_{new} = upperleftX_{old} \cos\theta - upperleftY_{old} \sin\theta$$

$$upperleftY_{new} = upperleftX_{old} \sin\theta + upperleftY_{old} \cos\theta$$

Then based on the new points simply get the subimage, which is the cropped rectangular region

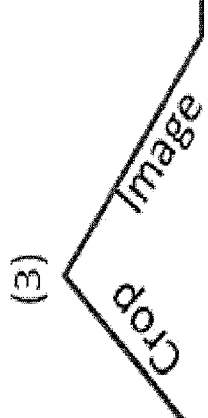
(3) Crop Image

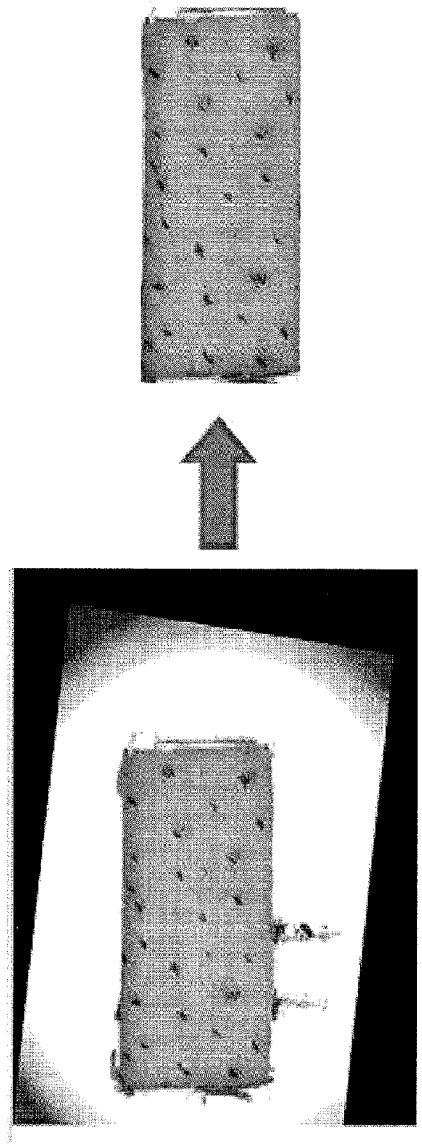

FIG. 17J (3) Approximation

Now we know the number of follicle points in each cluster. We can define the range to merge the follicle points. We observed that there are 1 to 5 follicle points detected for a single follicle. Similarly 6 to 10 points are detected for 2 follicles residing together. Using this approximation, we can define the other ranges for 3, 4, 5, and 6 follicles.

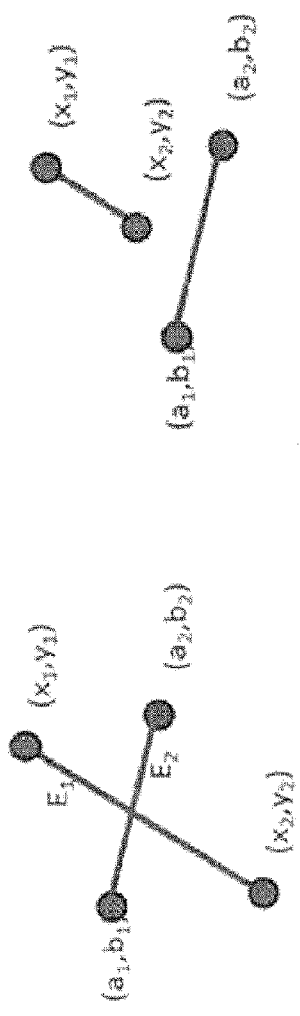

Case 1

Case 2

(2)

Edge Crossing Removal

To compute if two edges E1 and E2 are crossing, we need to know whether the endpoints of one edge are in the opposite sides of other edge. Let (x1,y1) and (x2,y2) be two endpoints of edge E1 and (a1,b1) and (a2,b2) are two endpoints of edge E2. Then the following two values, value 1 and value 2, will be of opposite sign (one will be '+' and other will be '-'), if (a1,b1) and (a2,b2) resides in opposite sides of edge E1.

$$value1=(x2-x1)*(b1-y2)-(y2-y1)*(a1-x2);$$
$$value2=(x2-x1)*(b2-y2)-(y2-y1)*(a2-x2);$$

This will work fine for case 1 in the above image. But this will not work for case 2 where the edges are not crossing each other, because still (a1,a2) and (a2,b2) are opposite sides of E1(x1,y1,x2,y2) and the above method will delete one of them, which is undesirable. So we need to consider another way to check if (x1,y1) and (x2,y2) are in the opposite side of edge E2 by following two equations.

$$value3=(a2-a1)*(y1-b2)-(b2-b1)*(x1-a2);$$
$$value4=(a2-a1)*(y2-b2)-(b2-b1)*(x2-a2).$$

Finally if value1 and value 2 are of opposite sign and value3 and value4 are of opposite sign, we are sure that they are involved in edge crossing. So we need to remove one of those.

Follicle Analysis Report (500)

HAIR TRANSPLANT INSTITUTE MIAMI

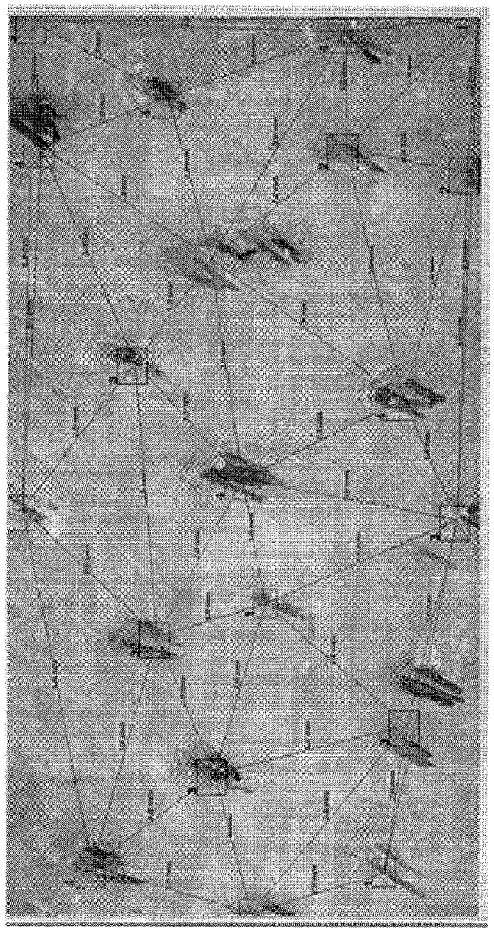

Patient No# 1000102
Age:42

Analysis Result#

| number of follicles | number of groups | percentage |
|---|---|---|
| 1 | 4 | 20% |
| 2 | 3 | 15% |
| 3 | 6 | 30% |
| 4 | 6 | 30% |
| 5 | 1 | 5% |

Inter Follicular Distance#
Mean# 2.10 mm
Max# 7.00 mm

Density#
Sample Area # 6.10 mm$^2$
Area Acquired# 2.10 mm$^2$
Area Analyzed# 1.05 mm$^2$
No of follicles per mm$^2$ # 2

Miscellaneous#
Bald Color # Reddish(190,76,44)
Follicle Color# Brown(190,106,104)

Comment:

Signature of Examinar

Signature of Verifier

CONTEXT BASED ALGORITHMIC FRAMEWORK FOR IDENTIFYING AND CLASSIFYING EMBEDDED IMAGES OF FOLLICLE UNITS

CROSS REFERENCE TO RELATED APPLICATIONS

This application is a National Stage Application of International Application No. PCT/US2014/063699, filed Nov. 3, 2014; which claims benefit of U.S. Provisional Application Ser. No. 61/898,836 filed Nov. 1, 2013; all of which are incorporated herein by reference in their entirety.

BACKGROUND OF INVENTION

Recent developments have increased the need for computerized analysis of biological images. Some of these types of biological images contain so much visual information, referred to as "noise," that most standard image computer analysis procedures cannot be applied to accurately detect desired objects. One example of such a noisy images are those of human hair and skin obtained through a microscope. The variations in skin texture, color, surface features, etc. make most image analysis procedures difficult to apply or provide inaccurate results. Of particular interest is the ability to analyze skin images to determine follicular counts and densities for use in hair transplant surgeries.

Qureshi and Bodduluri [1] developed a follicle detection model using contour. With their technique, a contour is drawn around the circumference of any detected possible follicle instance. If the contour has one concave hull, there are two follicles grown from same root. So the contour will look like a triangle with a concave hull. Similarly two concave hulls indicate three follicle units and so on. Unfortunately this method is only applicable to images where the follicle units does not overlap each other and where the follicle units is in good regular geometric shape like hair. If two or more follicles overlap or are crossed over each other, there will be more concave hulls, which will increase the error in counting of follicles. Also, if the image contains irregular shaped follicle units, the method will perceive more concave hulls on the contour.

TrichoScan is another system proposed by Hoffmann and Rolf [2] to count hairs on scalp images. This method detects straight lines on an image. These straight lines are considered to be individual hairs. To ensure accuracy, before the input image is acquired, a patient's hair is subject to a number of chemical treatment steps. These steps make the hair straight and prepares it for image analysis. After treatment and image acquisition, each straight line in the image is considered a hair instance in the image. This method is useful for some standard cases where the hair must be straight and hair edges must be smooth. However, if some hairs are crossed or overlapped with each other, there may be more hair lines counted than actually exist, or other anomalies in the data can occur.

Lempitsky and Zisserman [3] developed a supervised learning model to count objects in microscopic images. This method works well if there is similarity among the trained sets and input sets. Variation between trained sets and real input sets will cause errors. Unfortunately, most follicles in skin images are not similar and vary in size, color and geometric shape. So the learning method of Lempitsky and Zisserman is not very applicable and would require significant refinement to address the problem of follicular analysis of an image.

Thus, it can be seen that there is a particular need to be able to detect and count the number of follicles in a microscopic image of the scalp. An analysis to obtain an exact count of follicles in a given sample area is difficult not only because such images are noisy, but also the follicle shapes are nonstandard. Follicle objects can usually be detected in an image utilizing analysis based on RGB color codes. Unfortunately, follicles also overlapped, three or four of them can be tied together or growing from same root and fan out to different directions. Thus, distinguishing individual follicles or other structures in a visual image can be problematic.

BRIEF SUMMARY

In accordance with the subject invention, the difficulties of analyzing biological images to extract specific information about structures seen in the image is solved by the use of an algorithmic framework based on pixel group density to detect specific features. More specifically, the subject invention provides an algorithmic framework to accurately detect the number of hair follicles in a skin image.

One embodiment of the subject invention employs a pixel merging technique to connect the follicle pixels at one edge of a particular follicle to form small follicle articles and applied vicinity based clustering to group them together. Each group consists of a number of follicle particles. By applying scaling there is generated an approximate count of follicles in each group. This method is applicable to most of the real world images obtained from patients and can be divided into four sub systems:

1. A Feature Extraction Sub System: Extract the exact quadrilateral bald area from the input raw images.
2. Pre Processing Sub System: Filters the background scalp area to separate the follicular units from skin.
3. Follicle Detection Sub System: Detects each follicle unit uniquely by pixel merging, follicle particle building and clustering.
4. Inter Follicular Distance Sub System: Measures the inter follicular distances among the detected follicle clusters.

In general, a raw image is obtained from a patient utilizing microscopic techniques. Techniques and algorithms of the subject invention, which detect the corners of an image, are used to align the image and eliminate extraneous areas, to provide a uniform image area for analysis. The image is then analyzed for follicle pixels. The follicle pixels are merged to form follicle particles, which for purposes of analysis are considered to be the part of same follicle. The follicle particle data is then analyzed with a recursive 2D point clustering algorithm to group the merged follicle pixels into clusters. This analysis determines whether there are between two to seven merged follicle particles in a cluster for each follicle particle depending on the type of input image. Finally, scaling methods are applied to determine number of approximate follicles in each cluster.

More specifically, to begin analysis, it is necessary to extract or define only the scalp area to be analyzed in the microscopic image. Typically, the microscopic image provides a quadrilateral shaped scalp region. This quadrilateral region is not horizontal, which is necessary for follicular analysis. So, the first task is to rotate the image and extract the quadrilateral scalp area therefrom. Next, to rotate the image, the uppermost two corner points of the scalp region in the images can be detected. In one embodiment, the corners of the quadrilateral area are connected to the corners of the main image using virtual elastic threads. As with real elastic threads, the virtual elastic threads expand and/or contract to reach equilibrium, usually by minimizing the distance between each of the scalp area corners and the corresponding image corner to which it is attached. As a consequence, the image can be made horizontal. To achieve this equilibrium state for analysis with the subject invention, it is necessary to first detect the shortest thread.

Once the corners are obtained, the image can be rotated and the quadrilateral scalp area can be extracted. The follicle pixels can then be merged to form follicle particles, which are assumed to be the part of same follicle. This initial information can then be analyzed by a recursive 2D point clustering algorithm, which groups the merged follicle pixels into clusters. This further analysis results in two to seven merged follicle particles in a cluster for each follicle depending on the nature of input image. Then scaling was applied to decide the number of approximate follicles in each cluster.

Further, the inter object distances can be calculated by generating a graph, wherein only the neighboring vertices around a vertex are connected by edges without any edges crossing in the graph. One method for doing this is the Delaunay triangulation method. However, the Delaunay method can be more complex than necessary for the images to be analyzed. One embodiment of the subject invention employs a simple geometrical approach to generate a complete graph and remove unnecessary edges to obtain a clear mosaic output image. In another embodiment, the edges of the graph are designated with their lengths to provide inter object distances or, more specifically, the distance between each follicle particle, The methods of the subject invention provide a follicle count of acceptable accuracy on various images. The method can detect both long and short follicles regardless of their length, overlapped follicles, follicles growing from same root, follicles joined tightly together, and even broken follicles.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. Thus, understanding that these drawings depict only typical embodiments of the invention and are not therefore to be considered as limiting in scope, the invention will be described and explained with additional specificity and detail through the use of the accompanying drawings in which:

FIG. 10 is an illustration of the detect edge crossing method in one embodiment of the subject invention.

FIG. 11 is a schematic of one process for removing all edge crossings.

FIG. 16 is a table showing the results of analysis image samples using the methods of the subject invention.

DETAILED DISCLOSURE

Figure 1:
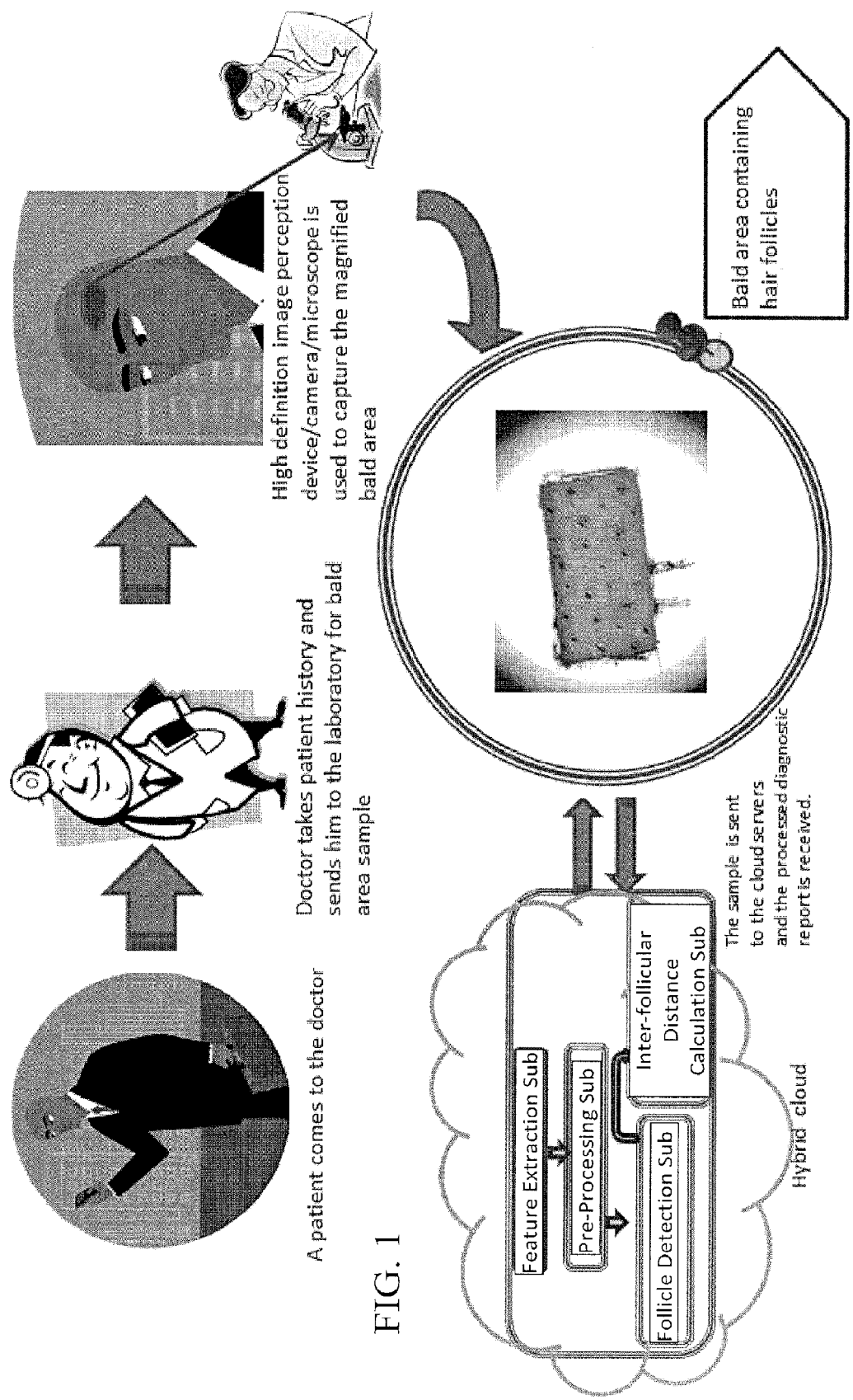
FIG. 1 is an illustration of an embodiment of the image acquisition and system initialization process of the subject invention.

The subject invention provides materials and methods for analyzing an image to detect specific features of interest within an image. More specifically, the subject invention provides methods and an algorithm by which to reduce the amount of extraneous information so that specific details within an image can be isolated and analyzed. In a specific embodiment, the subject invention provides a method by which a scalp sample image can be analyzed to detect the location and density of hair follicles in the sample. Once the location of individual hair follicles is determined, an algorithm of the subject invention can be used to provide metrics pertaining to follicle cluster and patterns.

The subject invention is particularly useful in the field of image analysis. In particular analysis of scalp sample images for use in formulating hair transplantation surgeries, still more particularly to automated processes for hair transplantation; however, a person with skill in the art will recognize other uses for the devices and methods of the subject invention. For example, images of other skin areas can also be processed and analyzed by the techniques described herein to provide metrics of interest for that particular area.

In a particular use, the methods described herein are used to detect and count the follicle units in the scalp sample images obtained from a patient having baldness. The scalp sample image is acquired through a microscopic imaging method using high definition image capturing devices. The images can be sent to a hybrid cloud where the image processing software resides. An image can be sent using either wired or wireless network. In wired network TCP, IP, Telnet, FTP protocol can be used to transfer the raw images to a cloud server. For a wireless network, a mobile phone can act as a smart client where GSM, CDMA protocols are used.

The embodiments of the subject invention can determine individual follicle groups, count the number of follicles in each group, and determine the inter-follicular distances between the follicle groups detected. Even images as noisy as those shown in FIG. 2 can be analyzed by the methods of the subject invention. The expected output image can be as shown in FIG. 3.

In the description that follows, a number of terms used in relation to image analysis and scalp images are utilized. In order to provide a clear and consistent understanding of the specification and claims, including the scope to be given such terms, the following definitions are provided.

The term "patient" as used herein, describes an animal, including mammals to which the systems and methods of the present invention are applied. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary, identification, or tracking purposes.

The term "noise" or "noisy" as applied herein refers to images that contain variations in brightness, color, pixel variations, or other information in addition to the information of interest. Typically, it is the noise in an image that inhibits accurate detection and/or analysis of information of interest.

Aspects of the invention can be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Any specific hardware devices, programming languages, components, processes, protocols, formats, and numerous other details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention can be practiced without these specific details. Computer systems, servers, work stations, and other machines can be connected to one another across a communication medium including, for example, a network or networks.

As one skilled in the art will appreciate, embodiments of the present invention can be embodied as, among other things: a method, system, or computer-program product. Accordingly, the embodiments can take the form of a hardware embodiment, a software embodiment, or an embodiment combining software and hardware. In an embodiment, the present invention takes the form of a computer-program product that includes computer-useable instructions embodied on one or more computer-readable media. Methods, data structures, interfaces, and other aspects of the invention described above can be embodied in such a computer-program product.

Computer-readable media include both volatile and non-volatile media, removable and non-removable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media, including memory storage devices and services, e.g., cloud environments. The computer-useable instructions form an interface to allow a computer to react according to a source of input. The instructions cooperate with other code segments or modules to initiate a variety of tasks in response to data received in conjunction with the source of the received data.

The present invention can also be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop or laptop computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touch-pad, touch-screen, or other pointing device, a keyboard, a camera, a monitor, a microphone, a speaker, a printer, a scanner, among other such devices. As further discussed above, the client devices can support various styles and types of client applications.

Figure 17A:
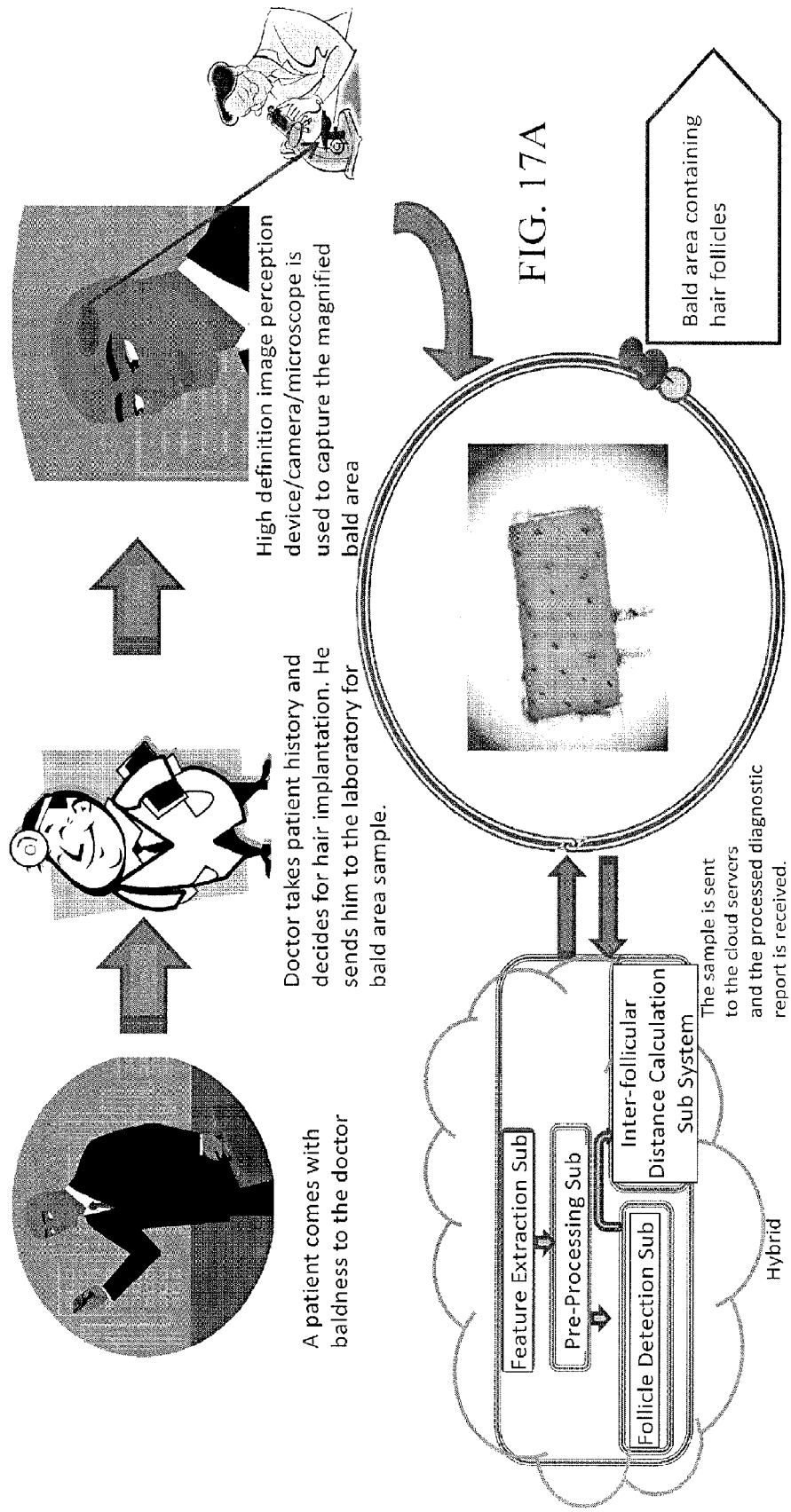
FIG. 17A illustrates an embodiment of the initialization step, according to the subject invention.
Figure 17E:
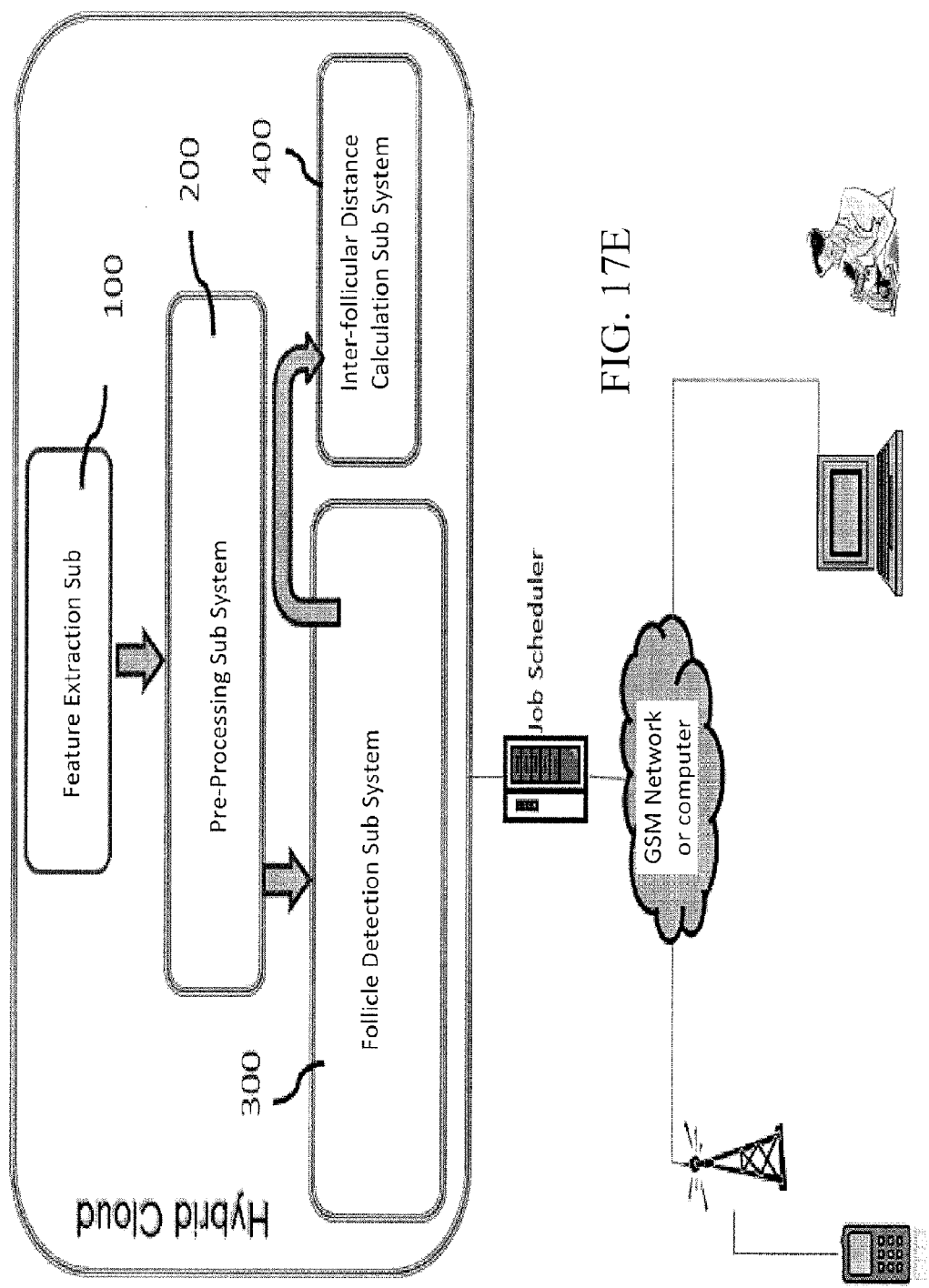
FIG. 17B illustrates an overview of the problem solved by the embodiments of the subject invention.
FIGS. 17C and 17D illustrate one embodiment of the sub-systems utilized in the subject invention FIG. 17E provides an overview of the steps employed by one embodiment of the subject invention.
FIG. 17F is a flowchart of the image analysis and graph generation steps of one embodiment of the subject invention.
FIGS. 17G, 17H, 17I, and 17J illustrate the steps pertaining to an embodiment of the Feature Extraction Sub System, according to the subject invention.
FIG. 17K is a flowchart illustrating one embodiment of the Pre-Processing Sub System, according to the subject invention.
FIG. 17L is photographs showing the results obtained by the steps shown in FIG. 17K.
FIG. 17M is a flowchart illustrating one embodiment of the Follicle Detection Sub System, according to the subject invention.
FIGS. 17N, 17O, and 17P show the results obtained at each step shown in FIG. 17M.
FIG. 17Q illustrates an embodiment of the Inter-Follicular Distance Calculation Sub System, according to the subject invention.
FIGS. 17R and 17S illustrate the steps involved in creating a graph providing the distances between each follicle in an image.
FIG. 17T illustrates one example of the results that can be obtained with the methods of the subject invention.
FIG. 17U illustrates one embodiment of a Follicle Analysis Report generated by the methods of the subject invention.
Figure 17F:
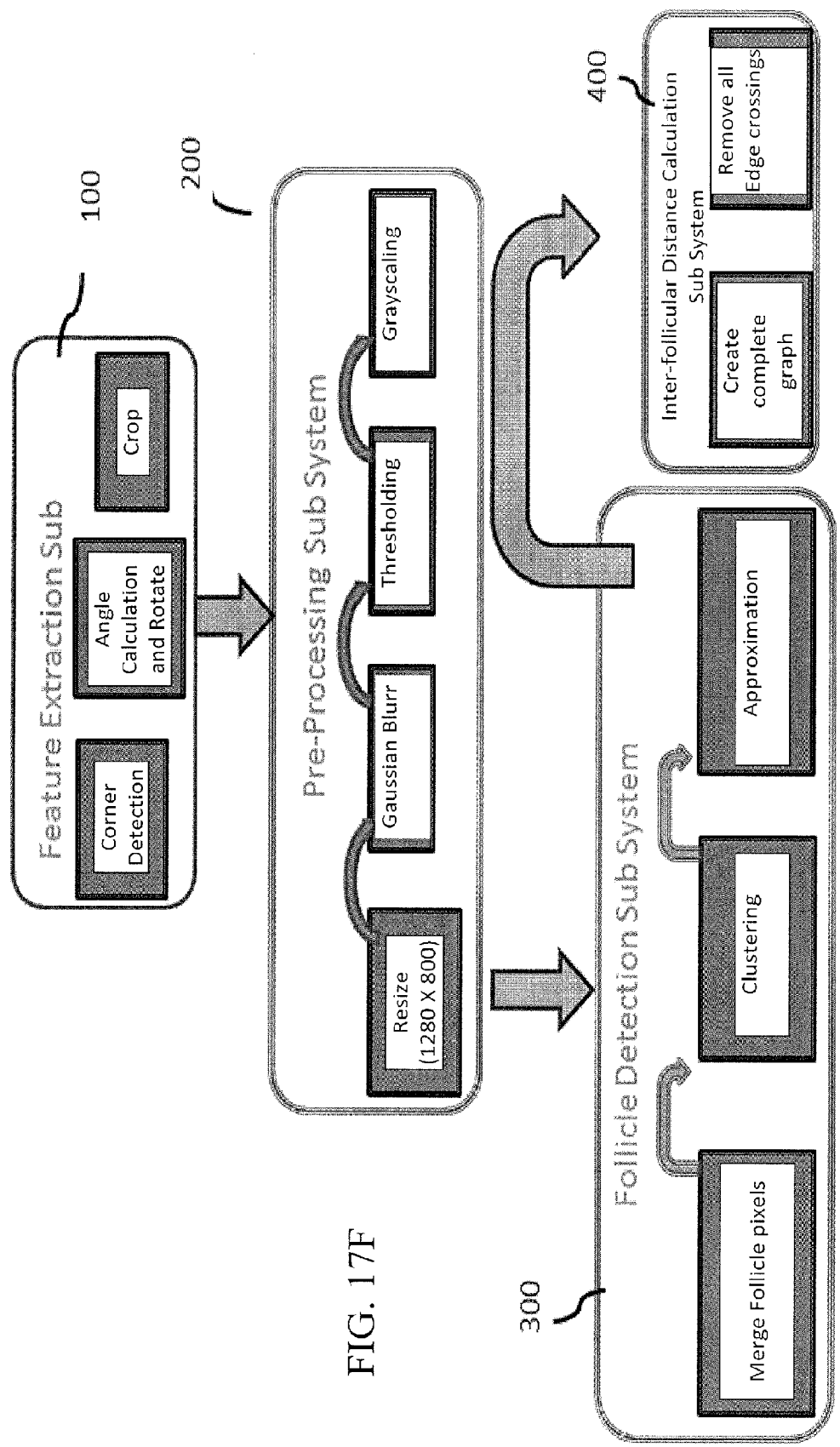
Figure 17G:
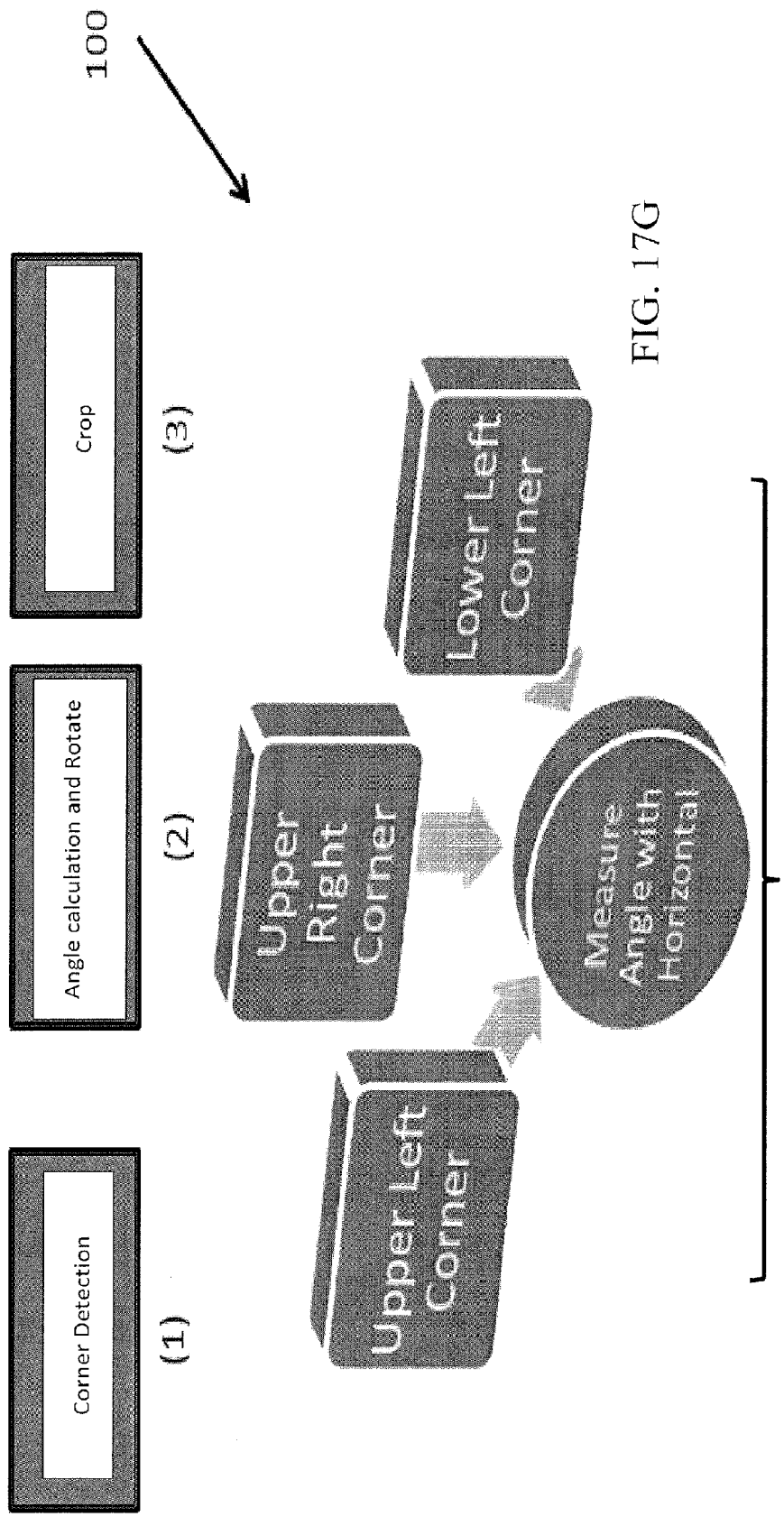
Figure 17K:
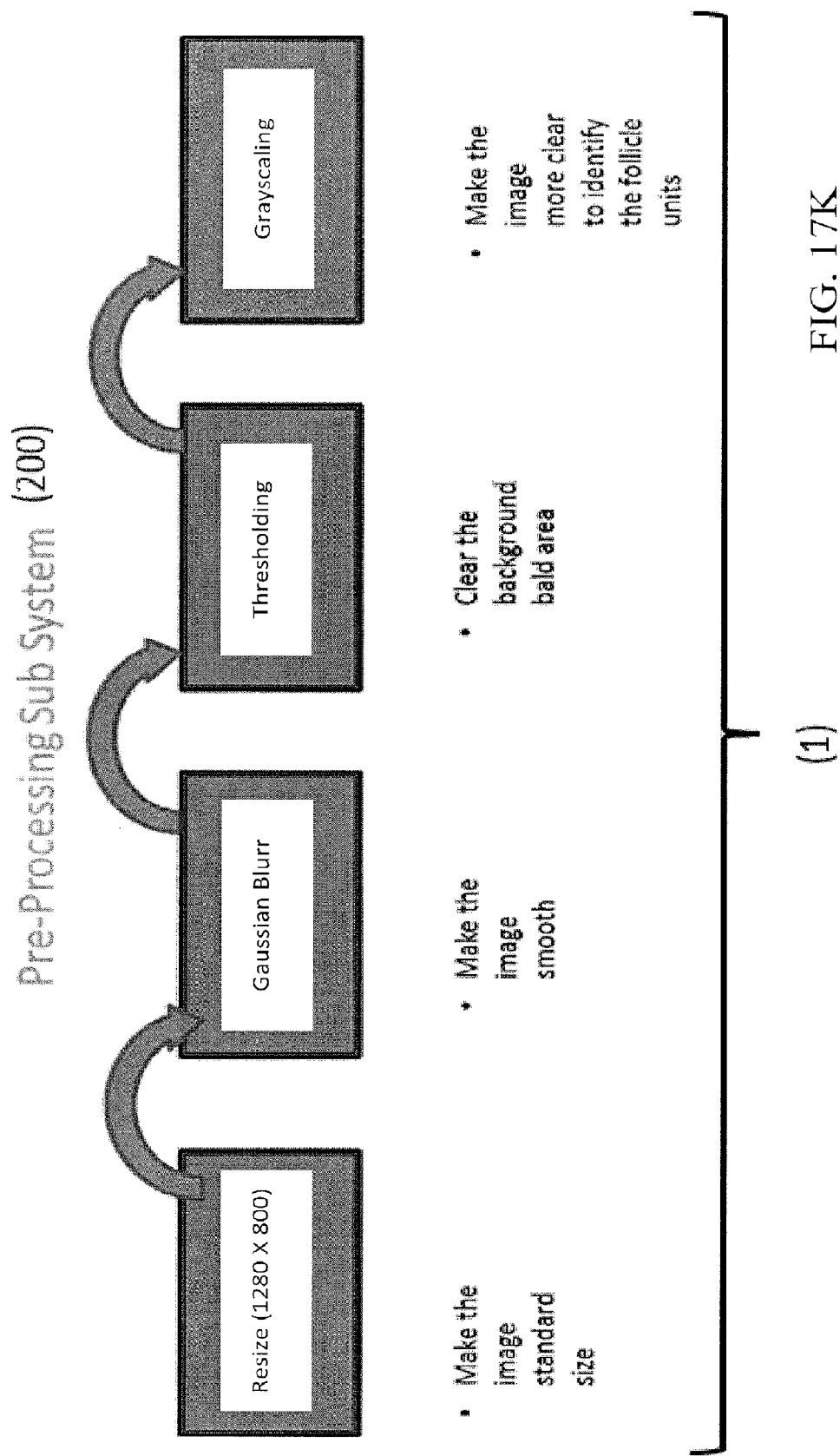
Figure 17L:
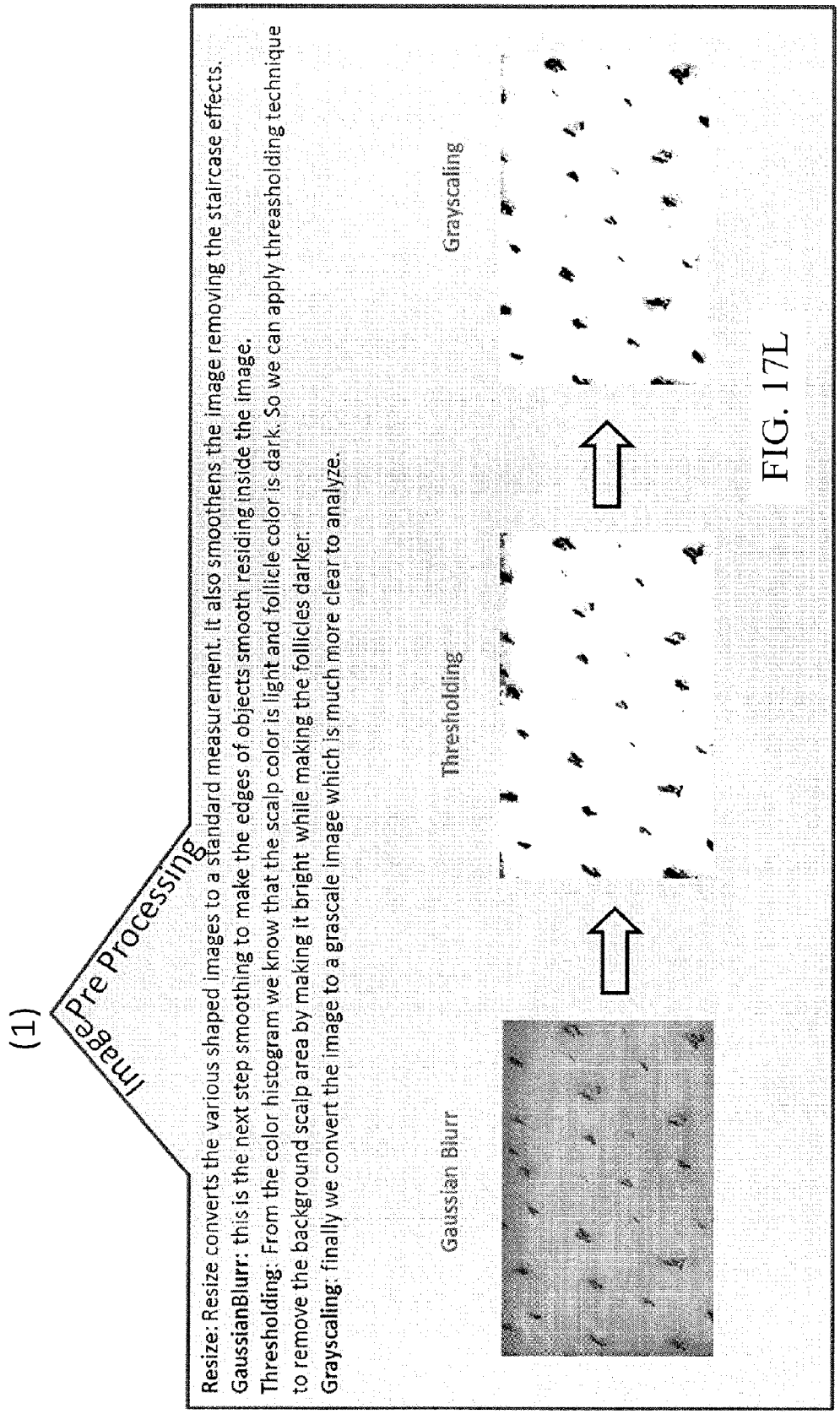
Figure 17M:
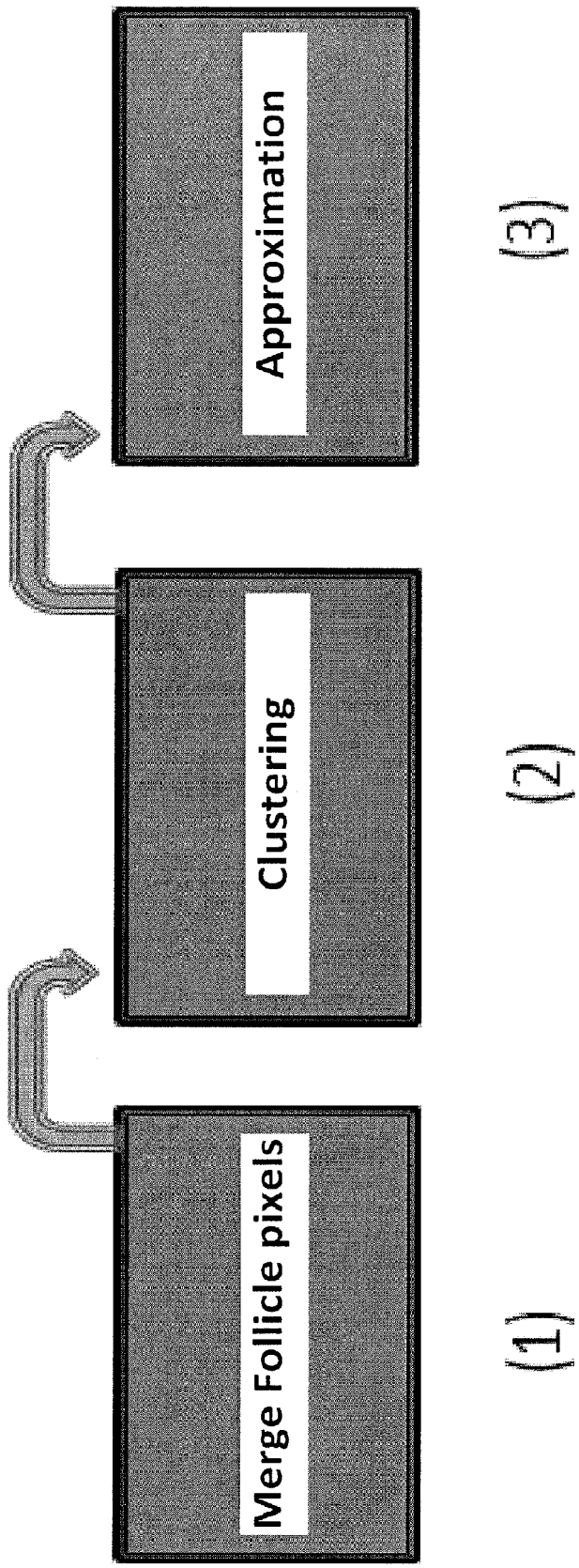
Figure 17N:
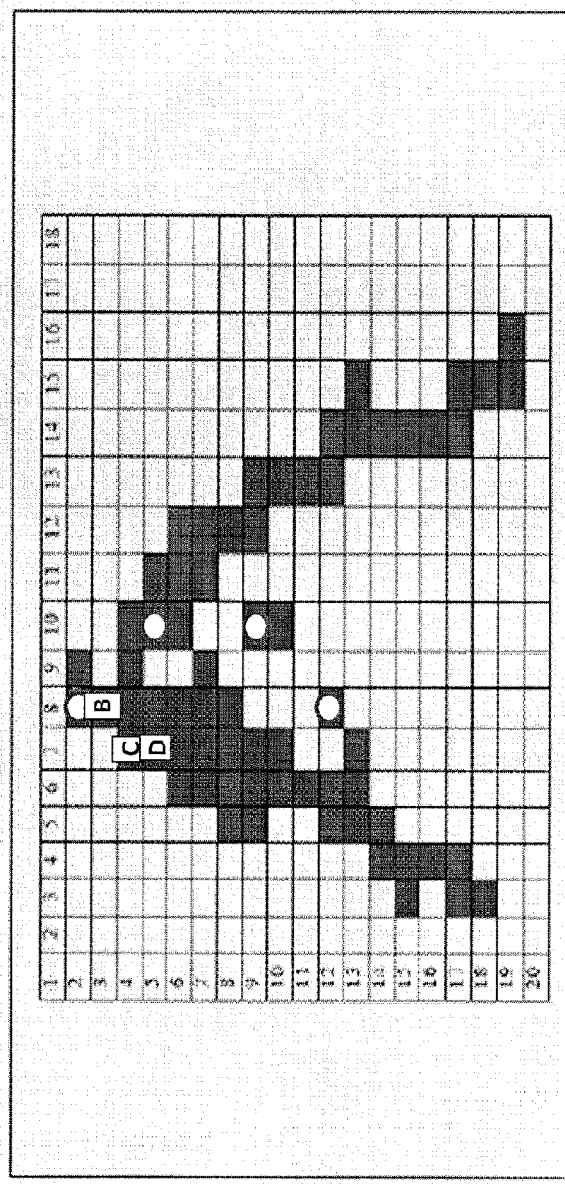
Figure 17O:
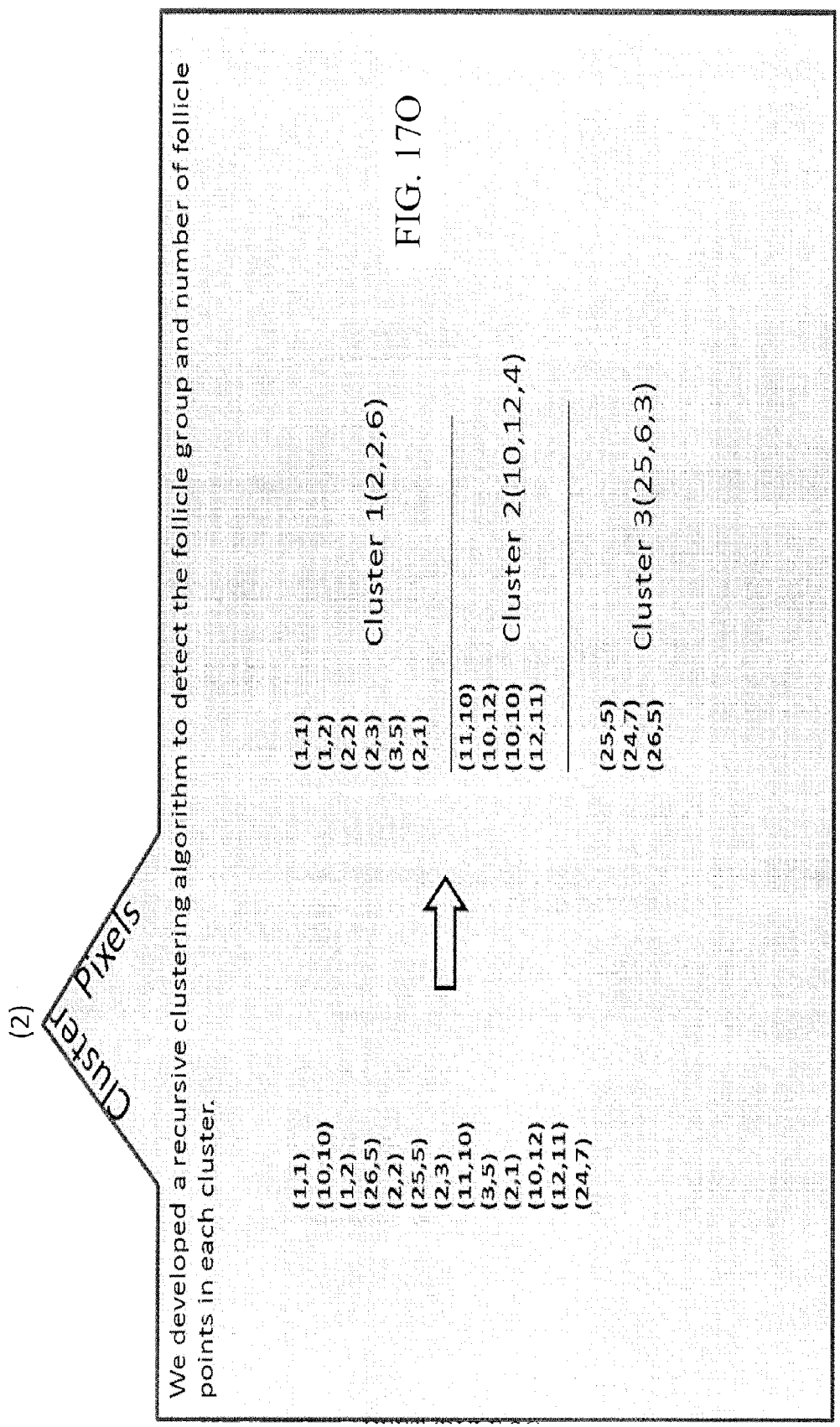
Figure 17P:
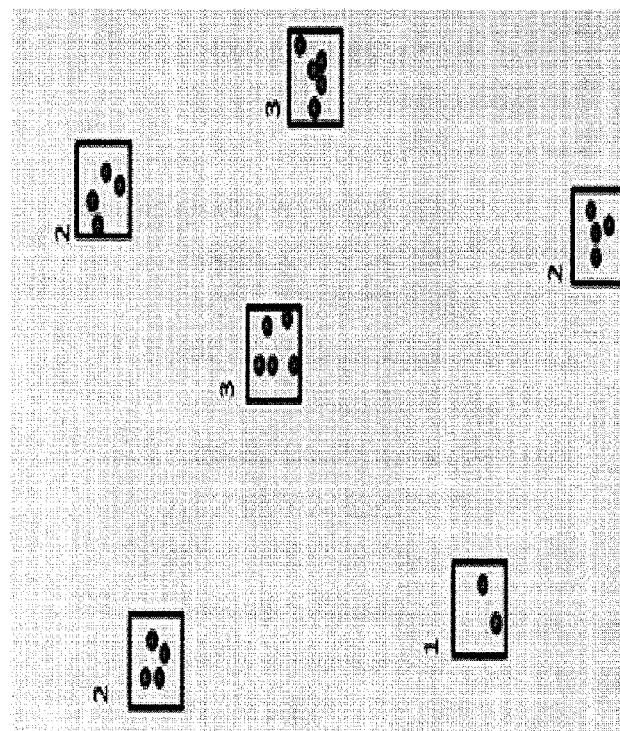
Figure 17Q:
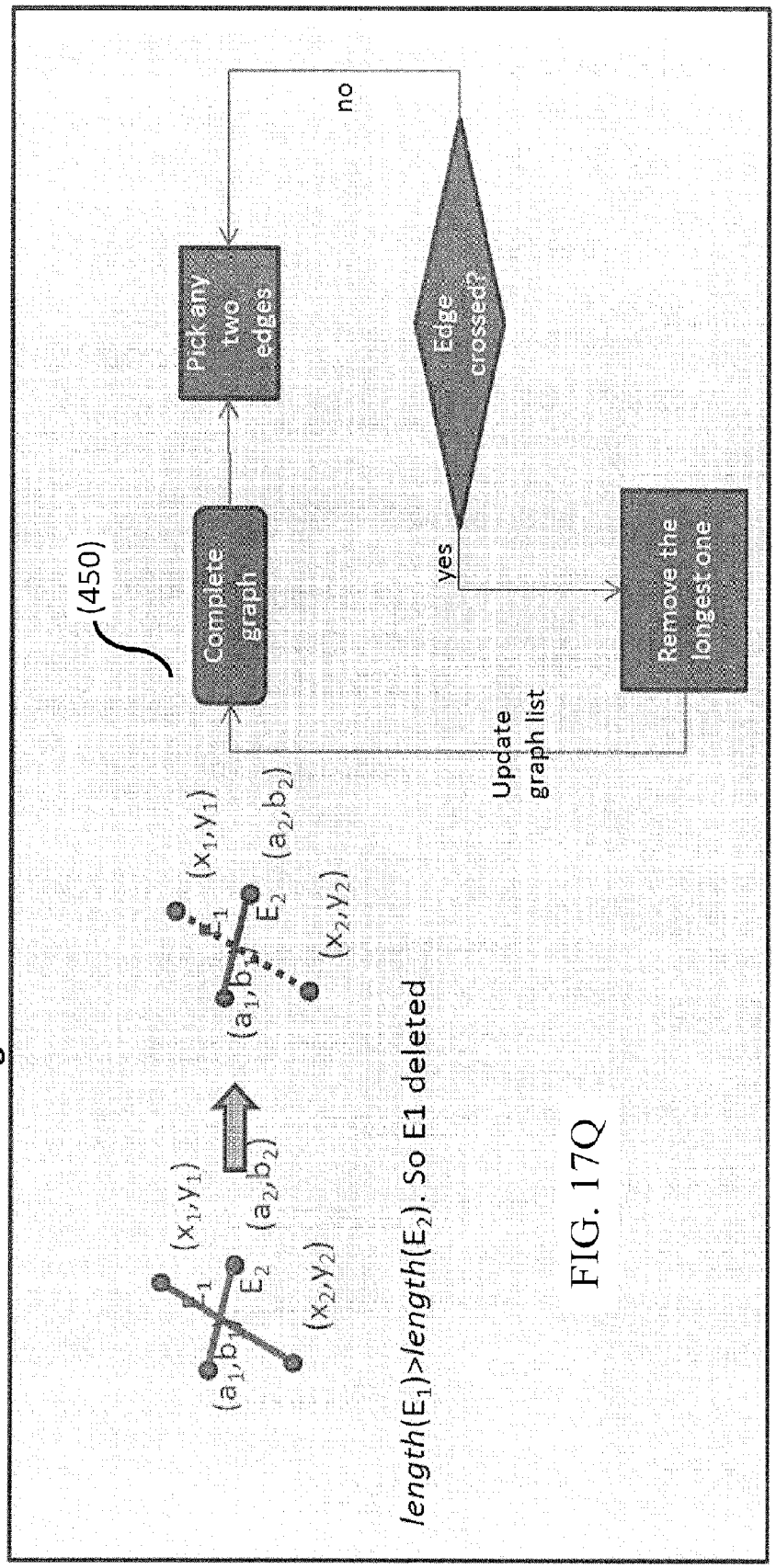
Figure 17R:
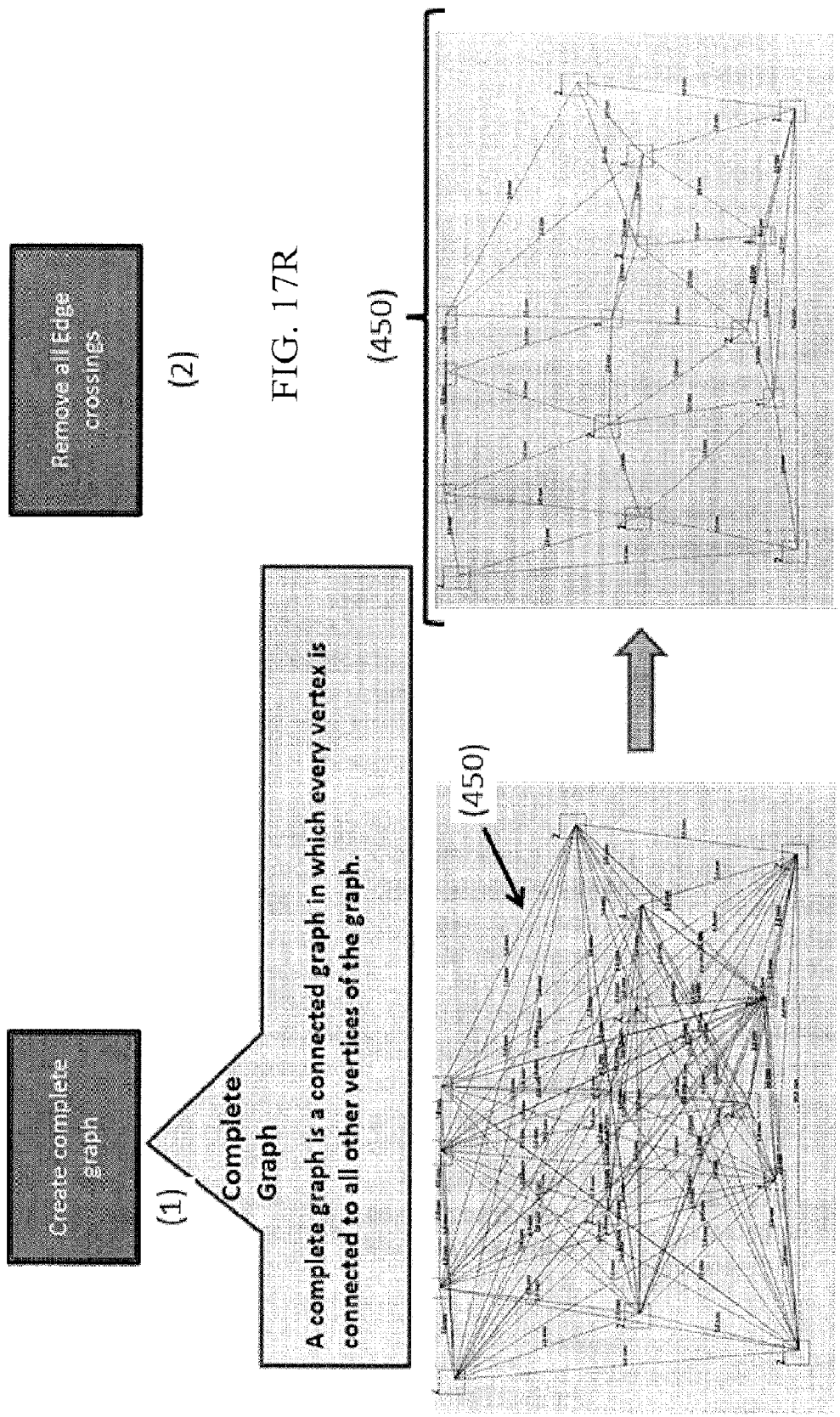

The description herein provides an embodiment of the steps and methods of the subject invention and FIGS. 17A through 17U illustrate one embodiment for practicing the subject invention within a particular operating environment. However, it will be understood that these steps and methods can be performed by a myriad of software and hardware configurations. Thus, the subject invention is not to be limited by the specific software and/or hardware mentioned herein.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Figure 5:
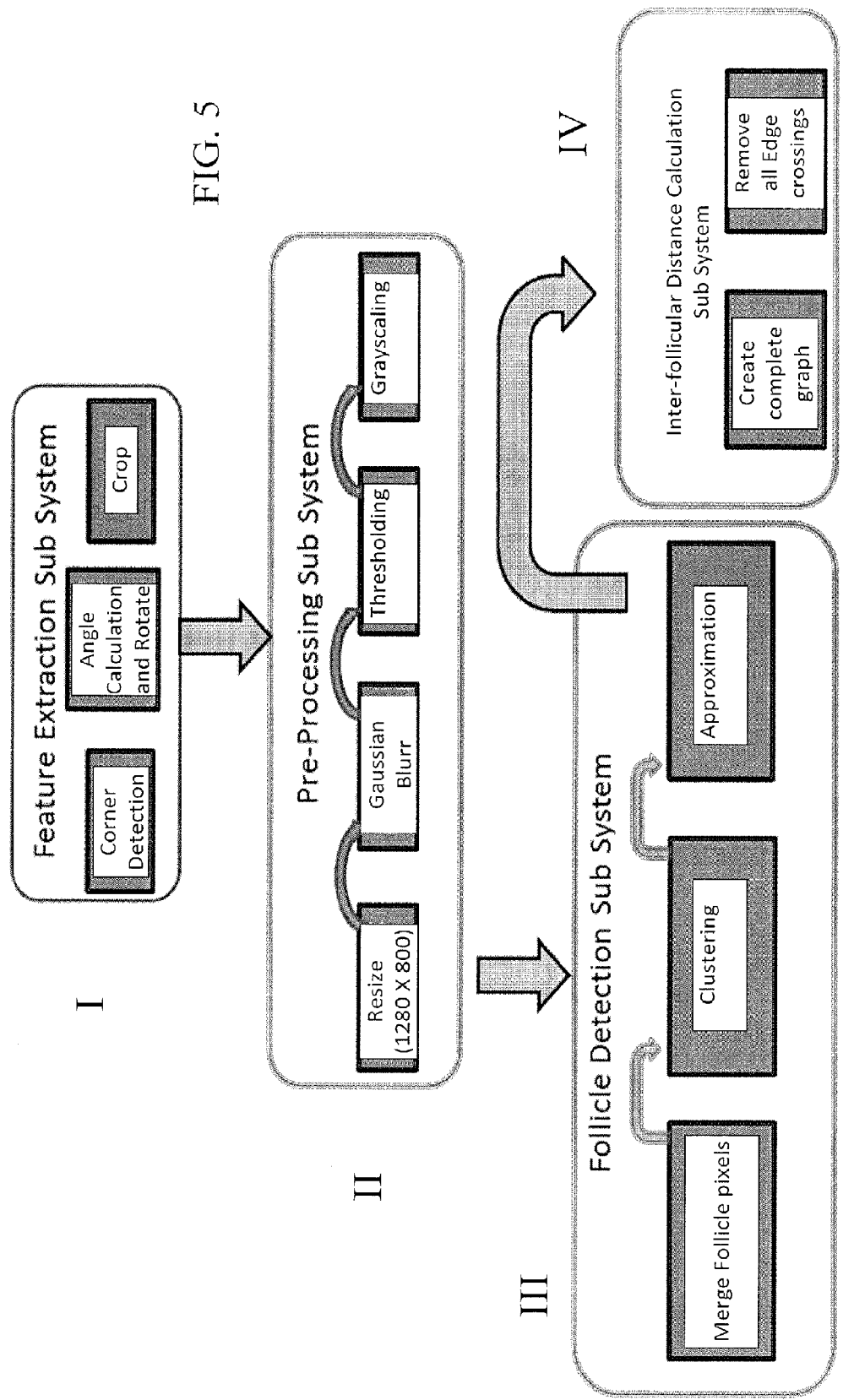
FIG. 5 is a flow chart illustrating a solution model and processing sub-system embodiment of the subject invention.

Reference will be made to the attached figures on which the same reference numerals are used throughout to indicate the same or similar components. With reference to the attached figures, which show certain embodiments of the subject invention, it can be seen that the subject invention comprises in general a Feature Extraction Sub System 100, a Pre-Processing Sub System 200, a Follicle Detection Sub System 300, and an Inter-follicular Distance Calculation Sub System 400. FIG. 5 is a flow chart that illustrates the general steps and procedures of the subject invention.

I. Feature Extraction Sub System (100)

A. Normalization and Generation of Intermediate Images

The normalization process of the subject invention is a process by which to extract the quadrilateral scalp region from an image. The scalp region of the image is considered the region of interest (ROI), as all the follicles reside within that area. Surrounding areas, such as the four edge regions around the quadrilateral scalp area, are removed as part of this step. In one embodiment, any three corners of the quadrilateral are detected and used to extract the sub-image. In another embodiment, the rectangular contour is directly detected.

For corner detection, the Harris corner detector method can be used, which measures the strength of detected corners, and only marks those above a given strength as an actual corner. Another method, based on the Canny and Hough algorithm, can be used to detect the rectangular contour of the ROI. It is also possible to use methods available through an openCV image processing library. It is possible that these methods will not provide the exact ROI or results of sufficient accuracy or consistency.

Figure 4:
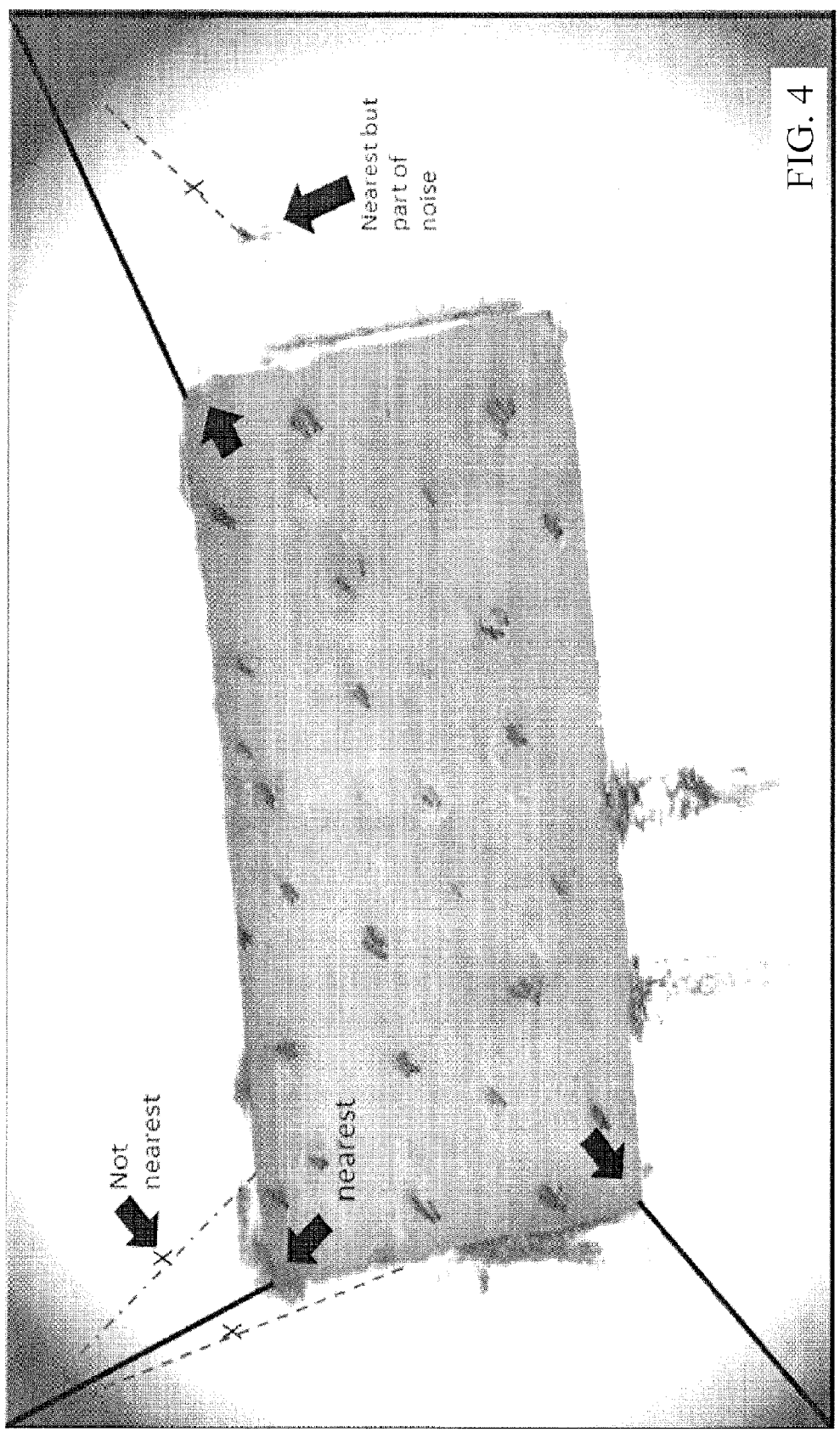
FIG. 4 is a photograph illustrating one embodiment of a "corner detection" method of the subject invention.

The methods of the subject invention employ a refined corner detection algorithm. Advantageously, the algorithm can detect the corners of the quadrilateral areas or ROI with approximately 90% accuracy. FIG. 4 shows the principle behind the corner detection mechanism of the subject invention.

Figure 2:
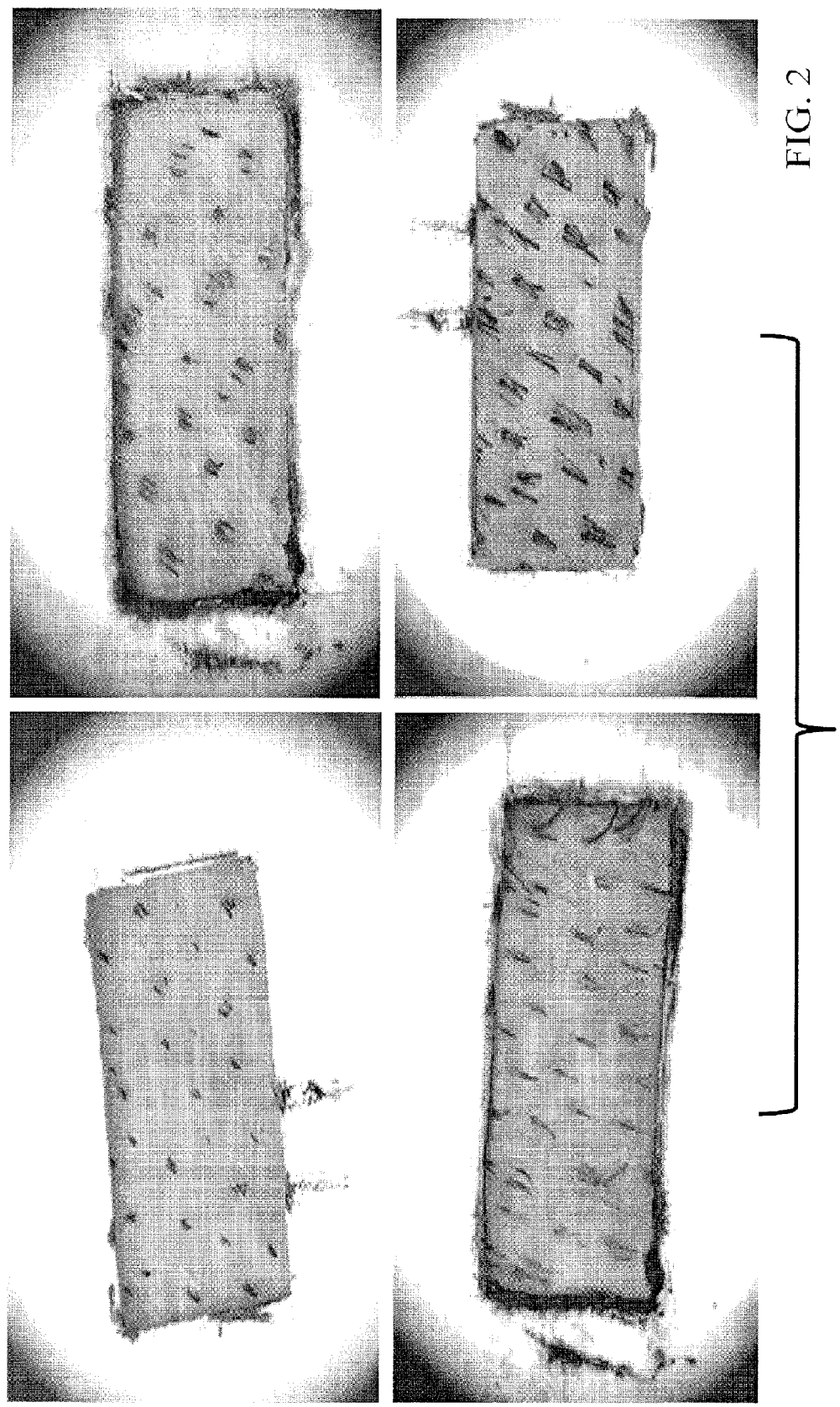
FIG. 2 is a series of photographs showing examples of input images that can be used with the embodiments of the subject invention.
Figure 3:
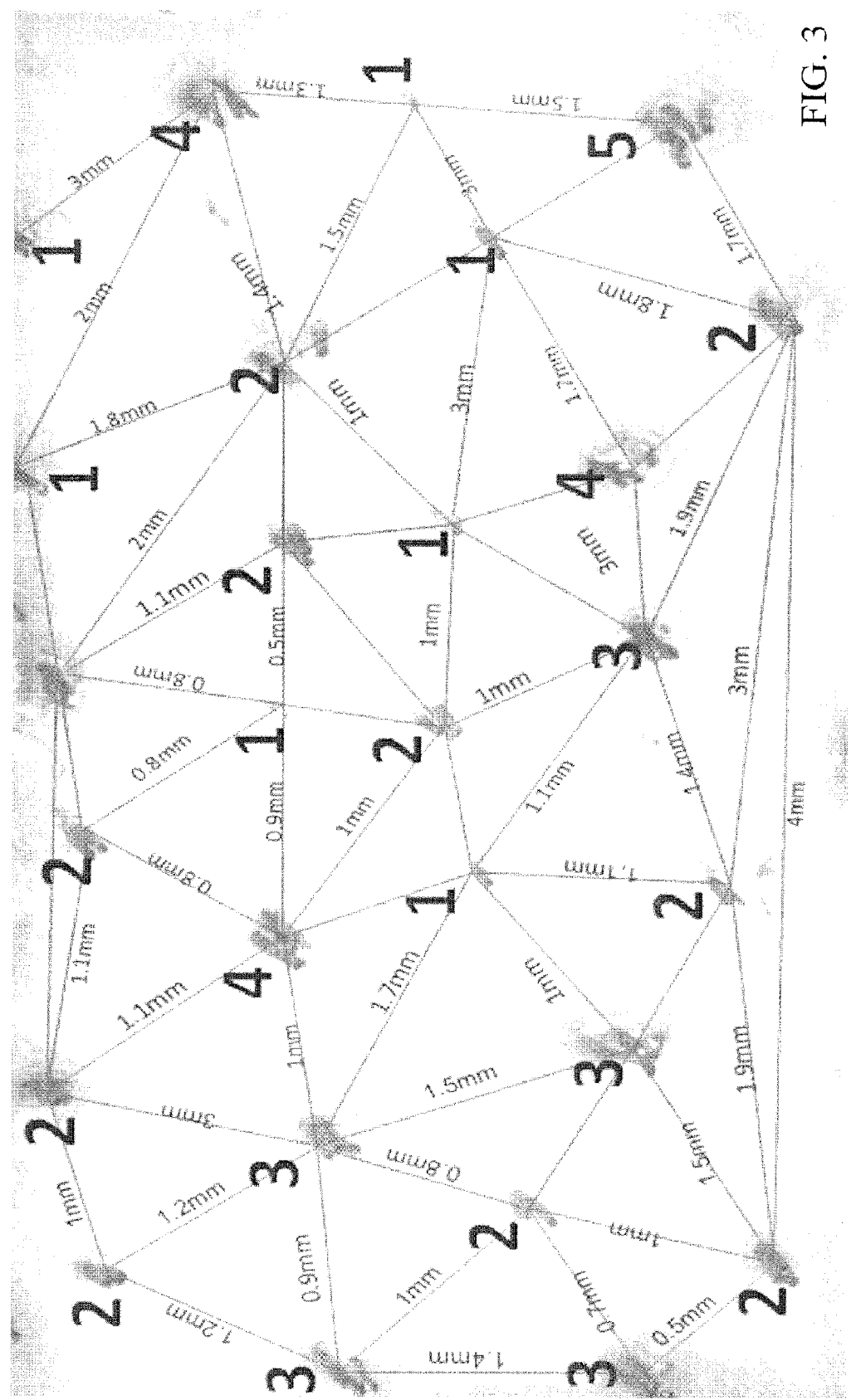
FIG. 3 is a photograph showing an output image generated by the methods of the subject invention.

In the method of the subject invention, an example of which is shown in Algorithm 1, the exact quadrilateral bald area from the input image, such as those shown in FIG. 2, can be extracted. For this, it is necessary to detect the corners of the quadrilateral scalp area. In one embodiment, the three corners—Upper left, Upper right, Lower left. The Lower right corner is then possible to detect though can be unnecessary. A further embodiment calculates the angle of the ROI with the horizontal axis being considered the upper left and upper right corners. The image is then rotated accordingly to make it horizontal. Once horizontal, the image can be cropped to create a sub-image of the exact ROI for further analysis.

B. Detect Corner

To detect corners, the ROI inside the raw input image is "tied" with a virtual elastic thread to the nearest corners of the raw input image. This means that the smallest thread connects the possible corner of the raw image with the corner of the ROI. This process is presented in FIG. 4. Noise in the raw image may cause the virtual elastic thread no to attach to an original corner, as shown in FIG. 4. To inhibit this reaction, the system of the subject invention checks some of the surrounding pixels in the image to determine whether the attachment point is a part of the ROI or is a part of image noise. If the possible corner is a part of ROI, then it is accepted that this as a corner, otherwise the system continues to search for another nearest pixel. In one embodiment, the image is analyzed with the method of the subject invention at least three times to find three corner co-ordinates. Ideally, the three coordinates correspond to the upper left, upper right and lower left corners of the ROI.

The upper left corner detection algorithm is shown in Algorithm 1.

Algorithm 1 FindCorner(IMAGE)

```
Input: An input Image I
Output: upperCornerX and upperCornerY
 1:  for y = 0 to I → height do
 2:      t = 0
 3:      for x = y to 1 do
 4:          pixel = (x,t)
 5:          t + +
 6:          red = pixel → Red( )
 7:          green = pixel → Green( )
 8:          blue = pixel → Blue( )
 9:          if [red,green,blue] > [230,230,230] then
10:              if [red,green,blue] = [scalpRed,scalpGreen,scalpBlue] then
11:                  if cornerTest(x,t) and nearest(0,0,x,t) then
12:                      upperCornerX = x
13:                      upperCornerY = t
14:                  end if
15:              end if
16:          end if
```

| Algorithm 1 FindCorner(IMAGE) |
| --- |
| 17:       end for |
| 18:   end for |

The other two corners can be found similarly. Using Algorithm 1, the image is scanned starting from (0,0). In the first run it scans (0,0) to (0,0) means one pixel; In the second run it scans (1,0) to (0,1). Similarly in the fifth run it scans (5,0), (4,1), (3,2), (2,3), (1,4), (0,5) pixels; The target of the scanner is to find a pixel that falls in the range of the scalp RGB color code, which is nearest to the corner of parent or raw input image. So the corner pixel is calculated using equation (1), shown below.

$$\text{upperleft}(x,y) = \min(\text{distance}(0,0,x_1,y_1),$$
$$\text{distance}(0,0,x_2,y_2), \ldots, \text{distance}(0,0,x_i,y_j)); \quad (1)$$

where $(x_i, y_j) \in$ Pixels(Rectangular Scalp Region)

C. Make the Image Horizontal and Crop Quadrilateral Area

Once the corner points have been determined, the image needs to be rotated to the horizontal. To crop an image, standard cropping tools known to those with skill in the art can be utilized. However, to do so requires providing a start point, height, and width of the target area to be cropped. With this information, a rotation angle can be determined utilizing equation (2):

$$\theta = \arctan\left(\frac{upperleftY - upperrightY}{upperleftX - upperrightX}\right) \times \frac{180}{\pi}. \quad (2)$$

Using an Affine transformation technique, the image can be rotated. The resulting image will be similar to that shown step B in FIG. 7. At this point, the upper left corner, lower left corner and upper right corner positions are known. After the Affine transformation technique is applied, the previously known positions of the three corners will be changed and relocated to a new position. It is necessary to determine the new coordinates of these three points. The new coordinates of the corners can be found using the equations (3)

$$upperleftX_{new} = upperleftX_{old} \cos\theta - upperleftY_{old} \sin\theta,$$
$$upperleftY_{new} = upperleftX_{old} \sin\theta + upperleftY_{old} \cos\theta. \quad (3)$$

One the new coordinates are determined, the new upper left corner co-ordinate becomes the starting point of the ROI. Similarly, the new upper right and lower left corner co-ordinates can be found using equations (3). Further, the width (distance of upper left and upper right) and height (distance of lower left and upper left) of the ROI can be determined to acquire the coordinates of the sub image or ROI, using these three parameters upper left (x,y), height and weight to crop the image. When complete, there will be provided a defined ROI comprising a rectangular scalp image, such as shown, for example, in step C of FIG. 7.

II. Pre Processing Sub System (200)

This part of the system of the subject invention can filter the background of the ROI to separate the follicular units and reduce the amount of noise in the ROI or make the ROI clean. This can be accomplished with standard noise filtration, smoothing, resizing and other standard image processing techniques known to those with skill in the art.

Reduce Noise and Make the Image Clear

Figure 6:
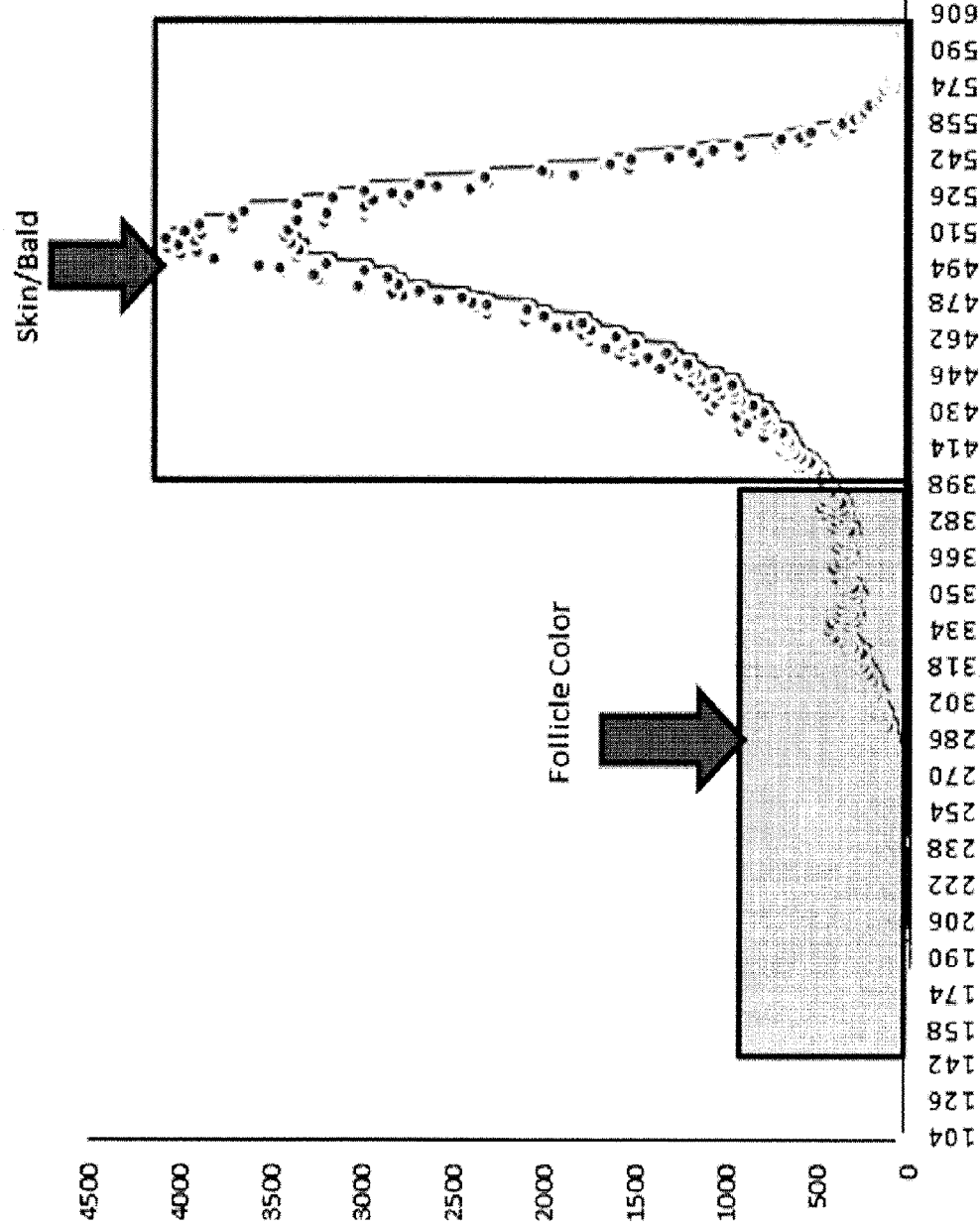
FIG. 6 is a histogram graph showing input image analysis results.

Next, the image needs to be resized and convert the input image size to a fixed standard size measurement for output. One more Gaussian Blurr smoothing operations can also be applied. These resizing and smoothing operations can make the image more compact, so that the image becomes smoother, removing some stairway shapes from edges of objects residing inside the image. Further, the follicle units need to be enhanced and clarified in the image. From the color histogram seen in FIG. 6 we know that the scalp color, for this patient, is light and the follicle color is dark for every sample image. A thresh holding, or contrast enhancing, technique can be applied to remove the background scalp area by making it brighter and making the follicles darker. Typically, if the intensity of a pixel is higher than a pre-defined threshold, the thresh holding technique can set the new pixel intensity to a maximum value (making them bright). Otherwise, the pixels are set to a value near zero (making them dark).

Figure 7:
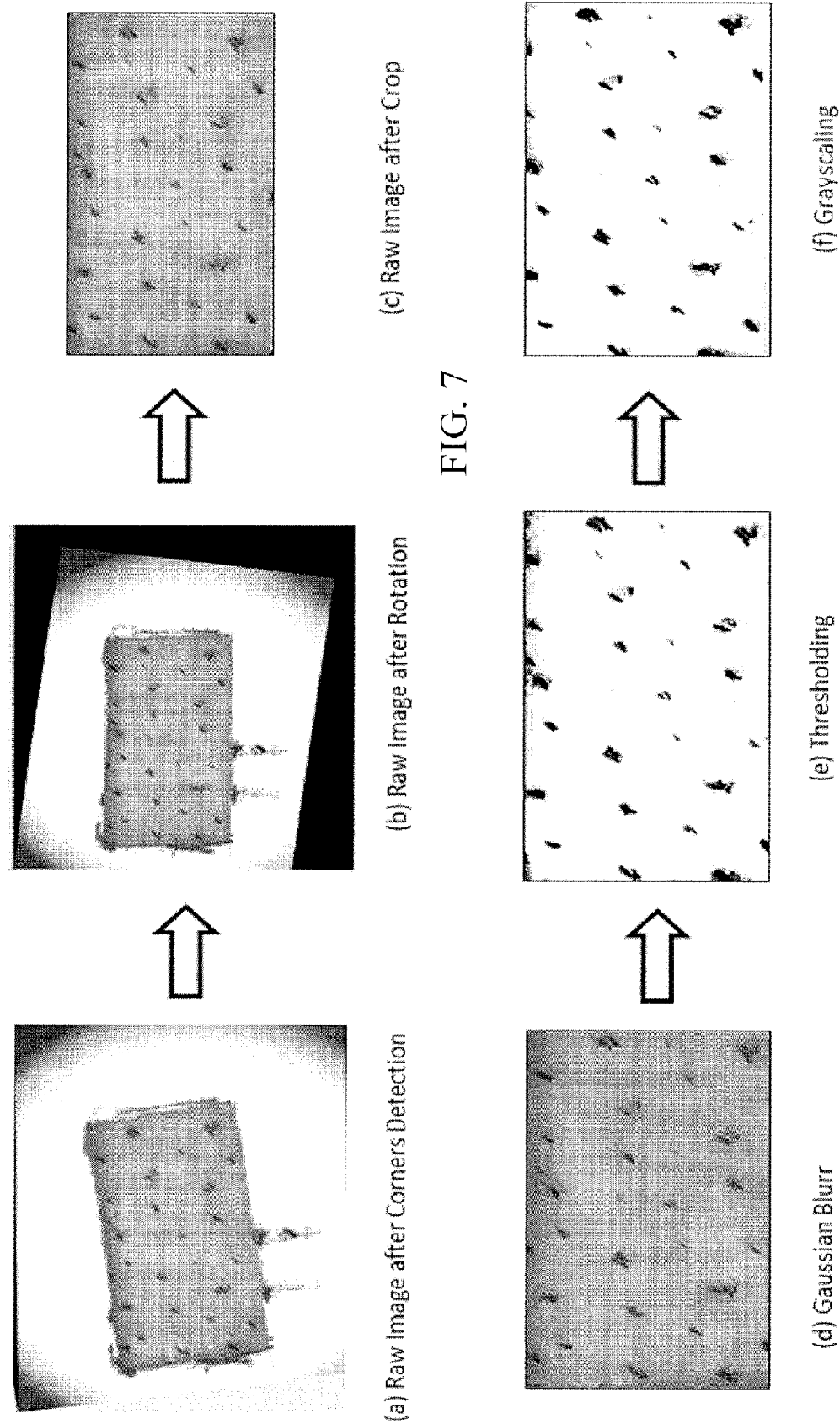
FIG. 7 is a series of photographs showing image normalization steps in one embodiment of the subject invention.
Figure 9:
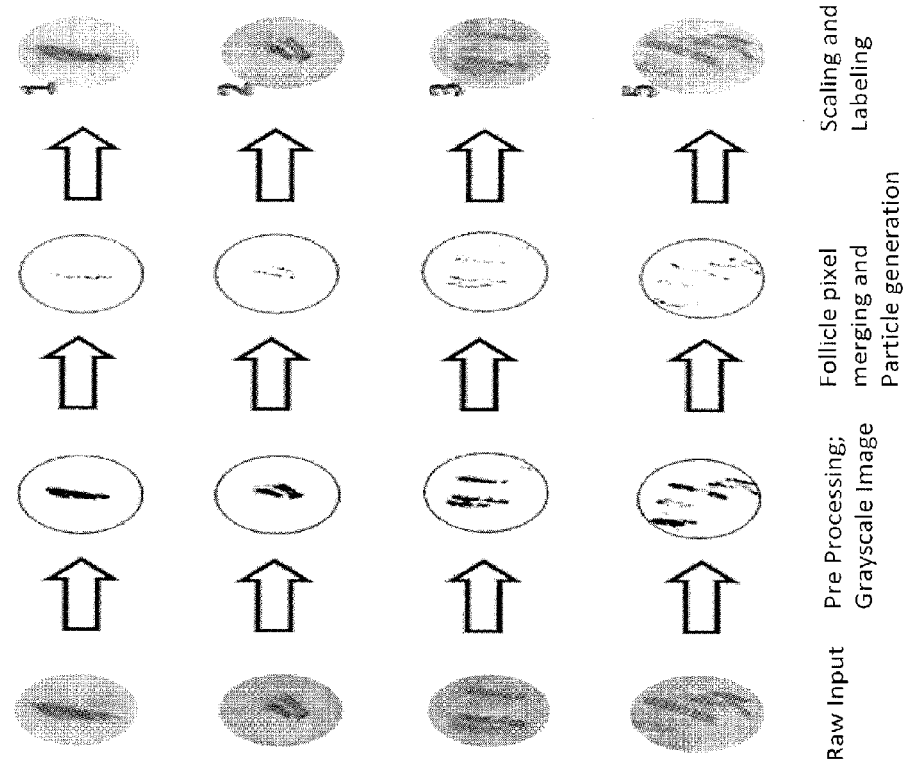
FIG. 9 is a series of photographs showing process of microscopic analysis and output obtained by the processing steps in an embodiment of the subject invention.

Once these steps are complete, the image can be converted to grayscale coloration. The increased contrast between features in the image, obtained by the above-described method, allows the grayscale image to be adjusted to contain mostly black and white pixels, increasing intensity and contract to make it clearer for analysis. This also makes only the border of scalp and follicles visible. If the border of scalp area are treated as image noise, these areas can be avoided from computations in the next steps. At this point, only the dark colored follicles are seen in the image, as seen in step I in FIG. 7. FIG. 7 illustrates the entire process of removing noise from an image. FIG. 9 shows examples of follicle images and the results of grayscale conversion.

III. Follicle Detection Sub System

To proceed, the system of the subject invention detects each follicle unit uniquely along with a 2D co-ordinate location for each follicle in the image. In one embodiment, the grayscale image is analyzed by a follicle detection and merging subsystem, which generates a number of small follicle particles for each follicle unit. A clustering algorithm can be applied to the follicle particles for grouping. After clustering analysis, the number of follicles in each cluster will be known, along with the 2D co-ordinates of the clusters.

A. Detect Follicles Pixel Group by Merging

The image can be scanned, usually from left to right, and searched for any dark regions, which would indicate possible follicles. The procedure is depicted, for example, in FIG. 8 and the process followed using Algorithm 2.

| Algorithm 2 DetectMergeFollicle(NormalizedIMAGE I) |
| --- |
| Input: An input Image I which has been normalized |
| Output: upperCornerX and upperCornerY |
| 1:   procedure detectMerge( ) |
| 2:     for y = 0 to I → height do |
| 3:         for x = 0 to I → width do |
| 4:             colorValue = I → getValue(x,y) |
| 5:             if colorValue = dark and follicleFound = false then |
| 6:                 if existingFollicleTest(x,y) is null then |
| 7:                     newFollicle → startXValue = newFollicle → endXValue = x |
| 8:                     newFollicle → startYValue = newFollicle → endYValue = y |
| 9:                     follicleList → add(newFollicle) |
| 10:               end if |
| 11:             else if colorValue = dark and folicleFound = true then |
| 12:                 do nothing |

| Algorithm 2 DetectMergeFollicle(NormalizedIMAGE I) |
| --- |
| 13:         else if colorValue = bright then |
| 14:            follicleFound = false |
| 15:         end if |
| 16:      end for |
| 17:   end for |
| 18:   End procedure |
| 19:   procedure existingFollicleTest(x,y) |
| 20:   for each follicle unit s ∈ follicleList do |
| 21:      if x − 1 = s → endXValue and y = s → endYValue then |
| 22:         s → endXValue = x;s → endYValue = y;follicleList → update(s);return s; |
| 23:      else if x − 1 = s → endXValue and y − 1 = s → endYValue then |
| 24:         s → endXValue = x;s → endYValue = y;follicleList → update(s);return s; |
| 25:      else if x = s → endXValue and y − 1 = s → endYValue then |
| 26:         s → endXValue = x;s → endYValue = y;follicleList → update(s);return s; |
| 27:      else if x + 1 = s → endXValue and y − 1 = s → endYValue then |
| 28:         s → endXValue = x;s → endYValue = y;follicleList → update(s);return s; |
| 29:      end if |
| 30:   end for |
| 31:   return null |
| 32:   End existingFollicleTest |

Figure 8:
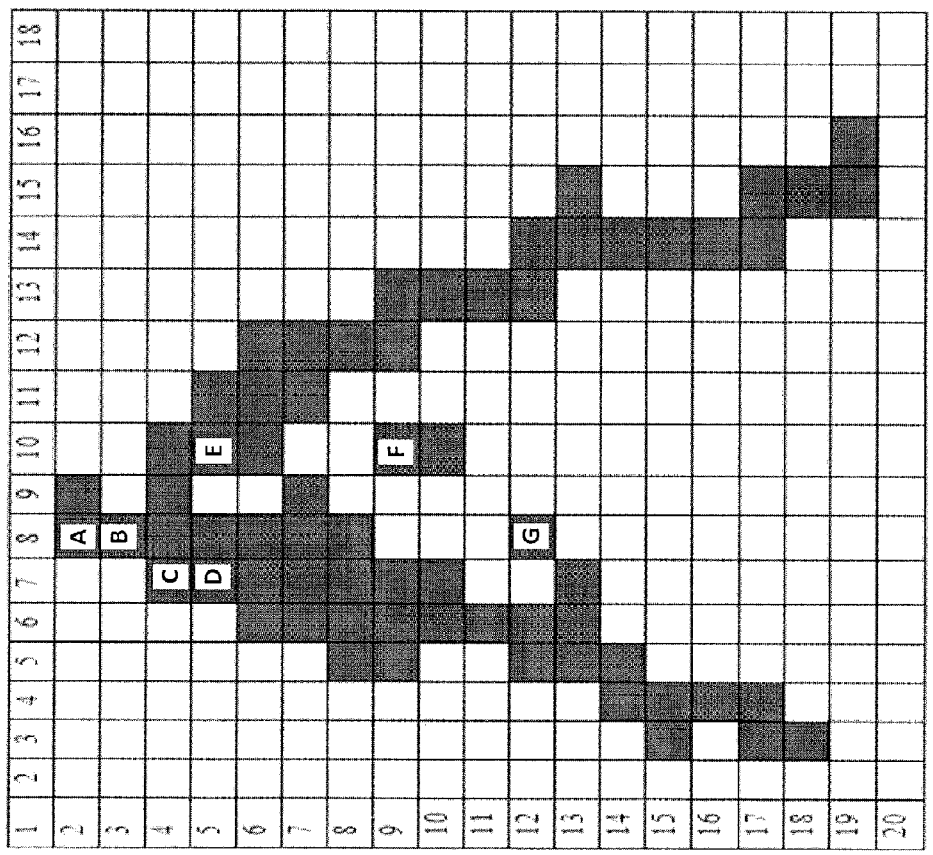
FIG. 8 is a chart showing a merge and count follicle pixel group.

Quick analysis can identify that there are two follicles seen in the image in FIG. 8. The follicles have started from a single root at A, coordinates (8, 2), and then became separate. In one embodiment, Algorithm 2 will start scanning the image from row 1 and column 1 It proceeds to scan columns 1 to 18 in row 1. Then it starts scanning row 2 from column 1 to 18, which is usually a left to right scan. When it reaches point A (8, 2) it detects a possible dark follicle pixel. Detection of a dark pixel presents two possibilities. The first is that the dark pixel is an instance of a newly detected follicle or, two it is the continuation of a previously detected follicle. To confirm this, the surrounding pixels can be examined. In a further embodiment, Algorithm 2 checks points (9,1), (8,1), (7,1) and (7,2), seen on the image in FIG. 8, to determine if any other dark pixels are connected. In this embodiment, it is only necessary to check four of the surrounding pixels during a scan of each row. For each follicle unit detected, a record of the start point or head pixel and endpoint or tail pixel co-ordinates is recorded. To determine if a newly detected dark pixel is a continuation of a follicle, the already detected follicles in surrounding four pixels can be analyzed. If a continuation of dark pixels is found in adjoining pixels, the endpoint or tail is updated with current pixel coordinates of the already detected follicle unit, for which the current pixel is treated as a continuation. With this method each follicle can start with one pixel and can grow by progression of continuation or tail pixels. If the four points (9,1), (8,1), (7,1) and (7,2) are bright and the follicle list is currently empty, the method records a new follicle by adding pixel A(8,2) to the follicle list with starting pixel (8,2). For each follicle recorded, the head and tail pixels are added to the follicle list. For the follicle just detected, the follicle head is (8,2). The follicle tail is also (8,2) as this is a newly detected follicle. Thus, initially, the head and tail are same. The first pixel is, $$P_0 = p_{(i,j)}; \quad (4)$$

where $\{p_{(i+1,j-1)}, p_{(i,j-1)}, p_{(i-1,j-1)}, p_{(i-1,j)}\} \notin$ GrayColor The algorithm proceeds to scan the next pixel (9,2). As seen in FIG. 8, it will also detect a possible follicle at this coordinate. However, according to the algorithm, once a follicle is detected, it is added to the follicle list. Then the algorithm ignores the consecutive pixels in same row until the scalp area in that row is completed, which means the end of a follicle region for current follicle in current row. The scan proceeds similarly in search of the other follicles. So the algorithm will not check and point (9,2), as it knows that it is the continuation of the previously detected follicle starting at A(8,2). This will continue until any bright pixel is not found which means the end of a follicle currently scanned by the system. With this strategy, pixel (10,2) is detected, it will ready the system to detect any new possible follicle. It can be seen that the rest of row 2 does not contain any possible follicle. So scanning row 2 is finished with a follicle detected from point A(8,2) to (8,2).

The algorithm then starts scanning row 3 and finds pixel (8,3) denoted by B in FIG. 8, as a new candidate follicle. So, this triggers the algorithm to check points (9,2), (8,2), (7,1) and (7,2) for any previously detected follicle tail or contiguous dark pixel. The algorithm detects and returns coordinates (8,2), as a previously detected follicle tail. So, the system recognizes point (8,3) as the continuation of a previously detected follicle and does not add it to the follicle particle list. But, an update is recorded as the follicle tail being (8,3) which was previously (8,2). The follicle head remains same, A(8,2). The rest of this row does not contain any follicle particles. Once scanning of row 3 is complete, the algorithm proceeds to build a follicle particle with a head A(8,2) and B(8,3). This represents follicle pixels merging to form a follicle particle.

In row 4 of FIG. 8, it can be seen that point C(7,4) is a follicle candidate. But after checking (8,3), (7,3), (6,3), (6,4), it is determined that point B(8,3) is a continuing follicle tail of one of the already detected follicles tail. This prompts the system to update that follicle particle to indicate that the tail of that follicle is now C(7,4). Then the pixels (8,4) to (10,4) will be omitted from follicle detection, as there is no white pixel in between them. Once updated with coordinates (11,4) the system is again ready to detect a new follicle.

By way of further example, scanning row 5, in FIG. 8, it can be seen that when existing follicle tail is updated with coordinates D(7,5), the system will avoid the pixels until (9,5) which is a white pixel. This also triggers the system that a new follicle has been detected and proceeds to find pixel E(10,5). It then checks the pixels (11,4), (10,4), (9,4) and (9,5). Since, as seen in FIG. 8, none of these coordinates is the tail of any detected follicle in the follicle particle list, this indicates that only one follicle has been detected so far in the image, whose tail is currently at D(7,5). The system will add a new follicle with head and tail at pixel E(10,5). Now, the image has two follicles detected. So follicle particles are now growing and after n steps, there will be a complete follicle particle $P_n$ where, as seen in Equation 5, $$P_n = P_0 \cup P_1 \cup P_2 \cup \ldots \cup P_k; \quad (5)$$

where $\{\forall p_i : i \neq 0 \land$
$\{\{p_{(i+1,j-1)} \in \text{GrayColor}\} \lor \{p_{(i,j-1)} \in \text{GrayColor}\} \lor$
$\{p_{(i-1,j-1)} \in \text{GrayColor}\} \lor \{p_{(i-1,j)} \in \text{GrayColor}\}\}$ In this way, after scanning the whole image, a total of four follicles is obtained starting at points A, E, F, and G. Similarly, tails or endpoints for each follicle are detected. At this point, these starting points and end points are recorded for next vicinity based clustering.

It can be seen in FIG. 8 that there are only two follicles indicated in that image. However, there were detected four follicle pixel groups/particles. This is due to the normalization process, in which some follicle pixels were lost.

Another reason is the image noise that occurs during sample acquisition from a patient. As a consequence some pixels or pixel groups became discrete from the original follicle image and erroneously form instances of new follicle particles. It can be seen that in FIG. 8, this happened at points F and G. One embodiment utilizes an "erode and dilate" procedure to eliminate this problem, which can minimize these gaps among the follicle pixel parts. However, this method can overcompensate and cause two or more separate, but very adjacent follicles, to be merged together and detected as one follicle. Nonetheless, this method provides a good approximation for the number of follicles, regardless of the variability in shape, thickness, or length. Follicles can lie in any direction with any angle irrespective to one another and will still be detected by the methods of the subject invention. With the algorithms disclosed herein, in general, multiple follicle pixel groups are detected for a single follicle. The next step is to perform clustering techniques to determine how many follicle particles are within a cluster.

B. Clustering of Follicle Group

At this point of the analysis process, a list of 2D points of follicle particles has been obtained, with only two points added in the follicle list for each follicle group, which indicate the start points and endpoints. The start pixel of each follicle particle can be used for clustering purposes. In one embodiment, a recursive clustering algorithm is utilized to cluster the 2D points. The algorithm is shown Algorithm 3. This algorithm takes the follicle list and gives a list of clusters of follicle pixel groups.

Initially, with the algorithm, there is a clusterList with n clusters containing one follicle group each. In each recursive step, two clusters are merged into one and the clusterList is updated. Then recursively merge another two clusters, then another two and so on. This recursion stops when there is no cluster remaining to be merged with some other cluster.

---

Algorithm 3 GenerateCluster (Collection of small clusters)

---

Input: A collection of 2D points which considered as small clusters
Output: aCluster
1:    mergingDone = false
2:    for all pt ∈ small clusters(2D points) do
3:        for all pt1 ∈ small clusters(2D points) do
4:           if pt(x,y) ≠ pt1(x,y) and distanceBetweenPoints(pt,pt1) < α then
5:               pt2(x,y) = newPoint(pt(x) + pt1(x)/2, pt(y) + pt1(y)/2)
6:               pt2(no of points in this cluster)=no of points in pt( )+no of points in pt1( )
7:               aClusterList → add(pt2)
8:               aClusterList → remove(pt)
9:               aClusterList → remove(pt1)
10:               mergingDone = true
11:               break
12:           end if
13:       end for
14:       if mergingDone = true then
15:           break
16:       end if
17:    end for
18:    if mergingDone = false then
19:       return aClusterList
20:    end if
21:    if mergingDone = true then
22:       return GenerateCluster(aClusterList)
23:    end if

---

C. Final Count of Follicles

The clusters and number of follicle pixel groups in a cluster is now available. In one embodiment, this count can be scaled to determine how many follicles there are in each cluster. There are various methods by which a proper scaling calibration can be determined. Usually, brute force analysis of multiple samples is conducted and results normalized for patient types. In one embodiment, this technique was used to develop the following scaling model for use in detecting the number of follicles. In this example, let ac be the number of merged follicle groups in cluster c.

$$numberof follicle N_c = \begin{cases} 1 & \text{if } 0 < \frac{a_c}{5} \leq 1 \\ 2 & \text{if } 1 < \frac{a_c}{5} \leq 2 \\ 3 & \text{if } 2 < \frac{a_c}{5} \leq 3 \\ 4 & \text{if } 3 < \frac{a_c}{5} \leq 6 \\ 5 & \text{if } 6 < \frac{a_c}{5} \leq 12 \\ 6 & \text{if } 12 < \frac{a_c}{5} \leq 30 \end{cases} \quad (6)$$

IV. Inter Follicular Distance Calculation

In this step, the inter-follicular distances among the detected follicle clusters or groups are measured. This can provide a connected points graph 450, such that all of the vertices (follicle groups) are connected only to respective neighbor vertices. Ideally, there are no edge (inter follicular distance) crossings.

A. Create a Complete Graph

Figure 13:
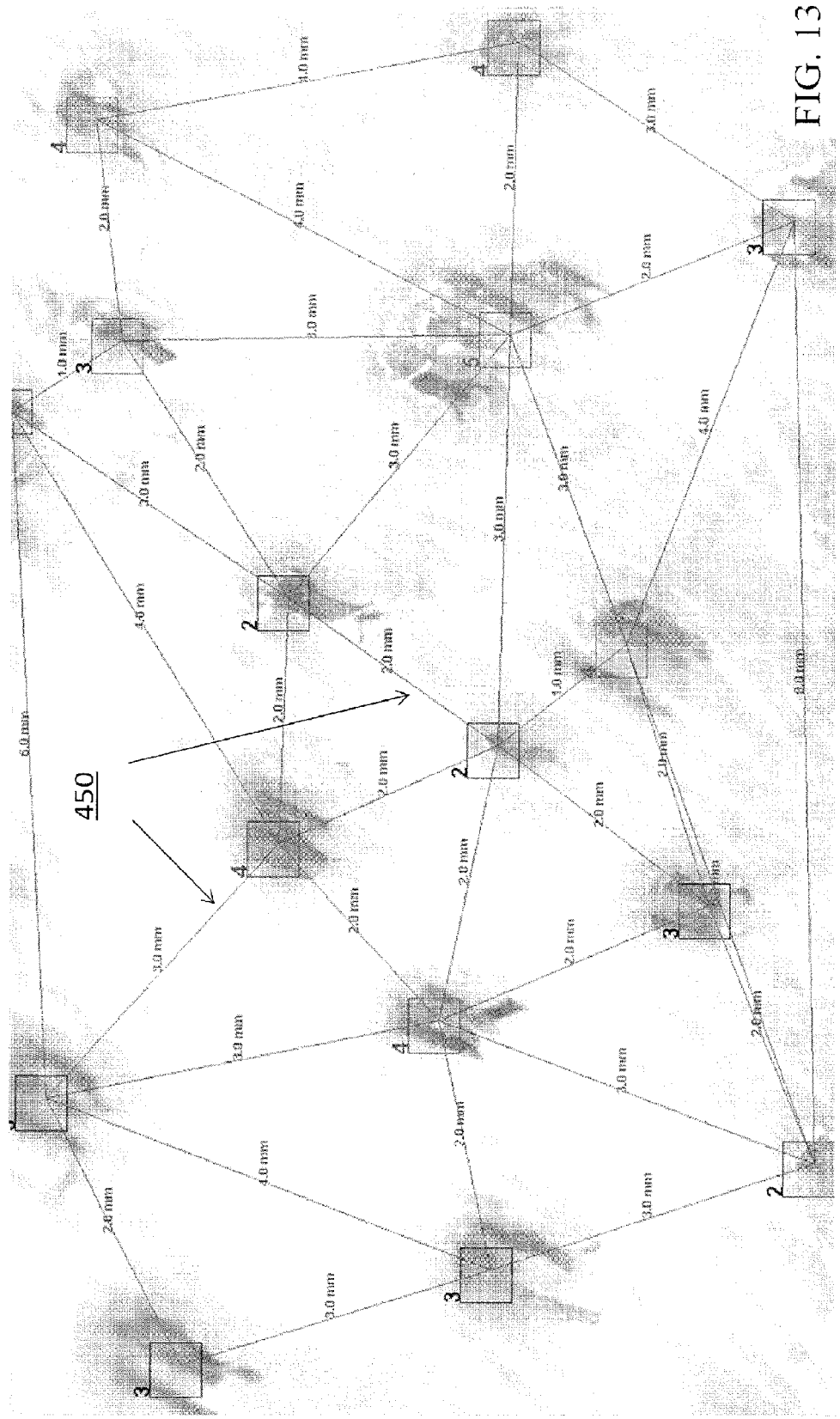
FIG. 13 is a photograph of an input image with an overlaid graph generated by the methods of the subject invention. In this image the follicles are not sufficiently dark.
Figure 14:
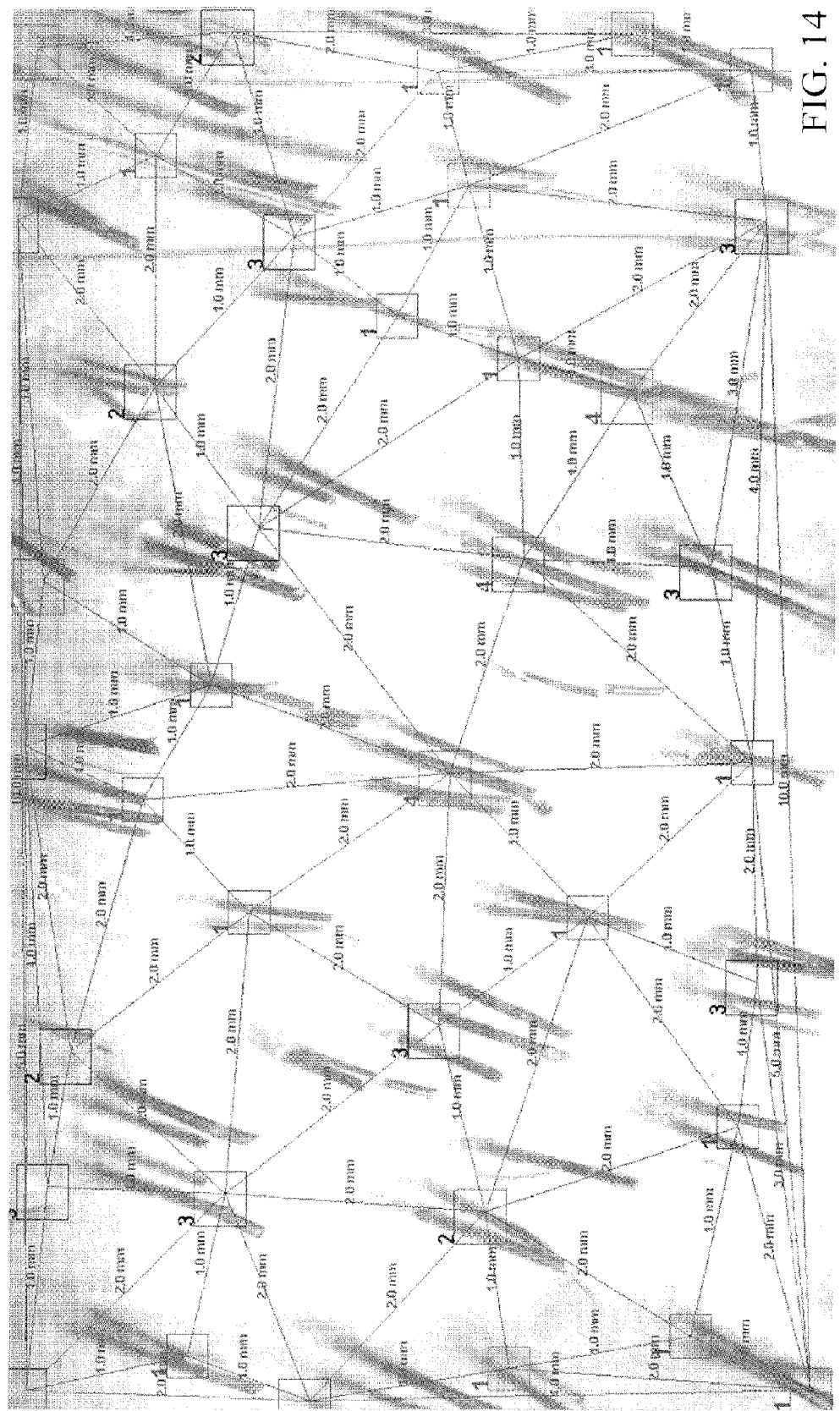
FIG. 14 is a photograph of an input image with an overlaid graph generated by the methods of the subject invention. In this image the follicles are dark but there is significant background interference or "noise."
Figure 15:
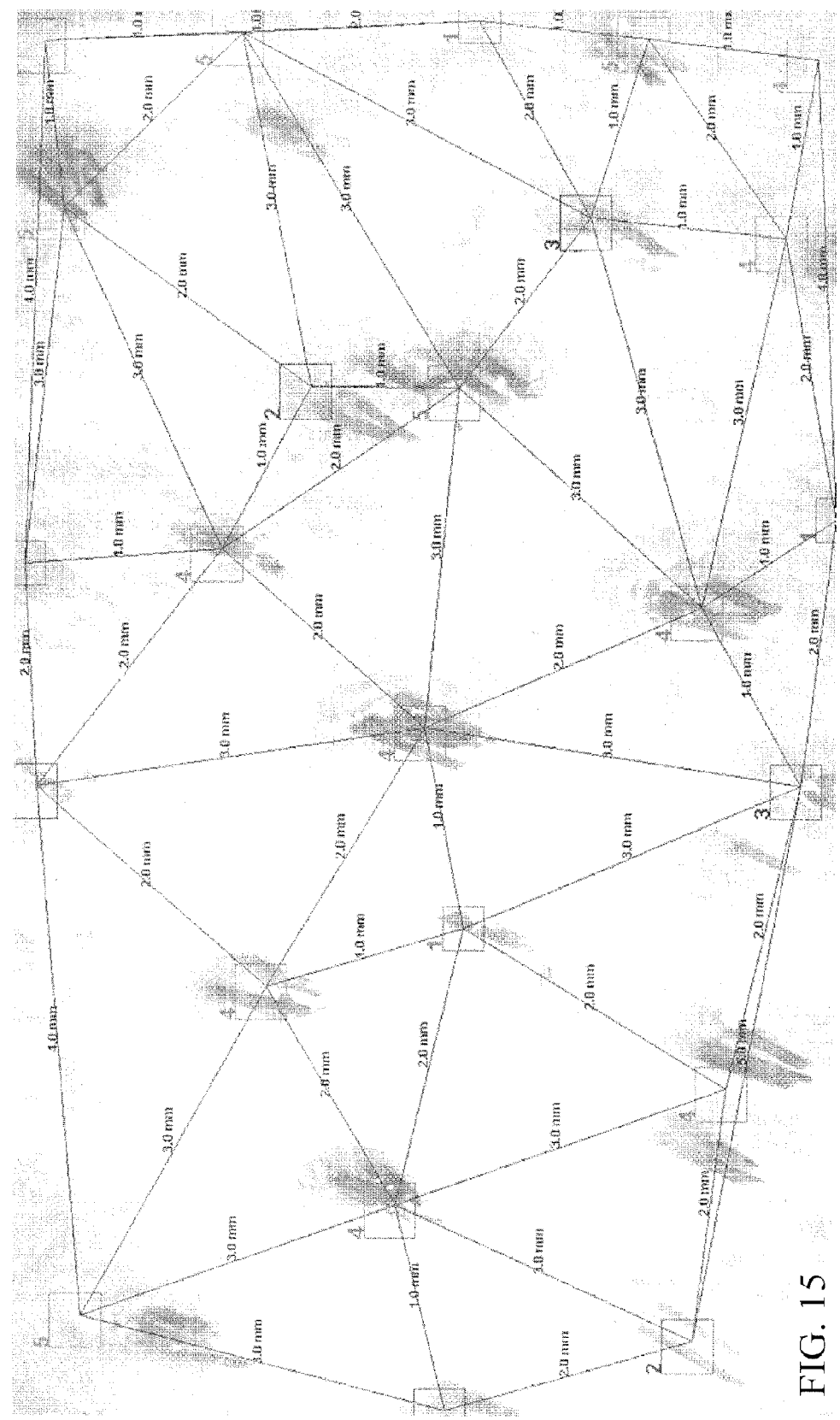
FIG. 15 is a photograph of an input image with an overlaid graph generated by the methods of the subject invention. In this image there is less "noise", providing better results.

Once the inter-follicular distances are determined, a complete connected points graph 450 can be created. A complete graph 450 will show every vertex connected to all other vertices of the graph. So, the edges from one follicle cluster to every other follicle clusters are drawn on the graph. FIGS. 13, 14, and 15 illustrate examples of images having different noise levels on which complete connected point graphs 450 have been drawn thereon.

B. Inter Follicular Distance Calculation

The next step is to remove all of the edge crossings. To compute if two edges, such as E1 and E2, are crossing, it is necessary to know whether the endpoints of one edge are in the opposite sides of the other edge. By way of example, let (x1,y1) and (x2, y2) be two endpoints of edge E1 and (a1,b1) and (a2,b2) be two endpoints of edge E2. This would indicate that the following two values, value1 and value2, will be of opposite sign (one will be + and other will be −); if (a1,b1) and (a2,b2) resides in opposite sides of edge E1.

value1=(x2−x1)×(b1−y2)−(y2−y1)×(a1−x2);

value2=(x2−x1)×(b2−y2)−(y2−y1)×(a2−x2);    (7)

With reference to FIG. 10, it can be seen that this is acceptable in case 1. But, this will not work for the case 2, where the edges are not crossing each other; because (a1,a2) and (a2,b2) are on opposite sides of E1(x1,y1,x2,y2) and the above method will delete one of them. But, it would be unacceptable to remove any point in case 2. Thus, it can be necessary to consider another method by which to check whether (x1,y1) and (x2,y2) are in the opposite side of edge E2. One embodiment, utilizes the following two equations (8).

value3=(a2−a1)×(y1−b2)−(b2−b1)×(x1−a2);

value4=(a2−a1)×(y2−b2)−(b2−b1)×(x2−a2);    (8)

With these equations, if value1 and value 2 are of opposite signs and value3 and value4 are of opposite signs, it can be accurately assumed that they are involved in edge crossing, requiring that one be removed. In one embodiment, the longer edge between these two edges is removed, so that a connected points graph 450 connecting the nearer neighboring vertices can be created.

This process can be carried out until all of the edges involved in crossing have been removed. FIG. 11 shows a flow chart of this edge clearing step.

C. Follicle Design Patterns and Mobile Application Development for Automation

Figure 17T:
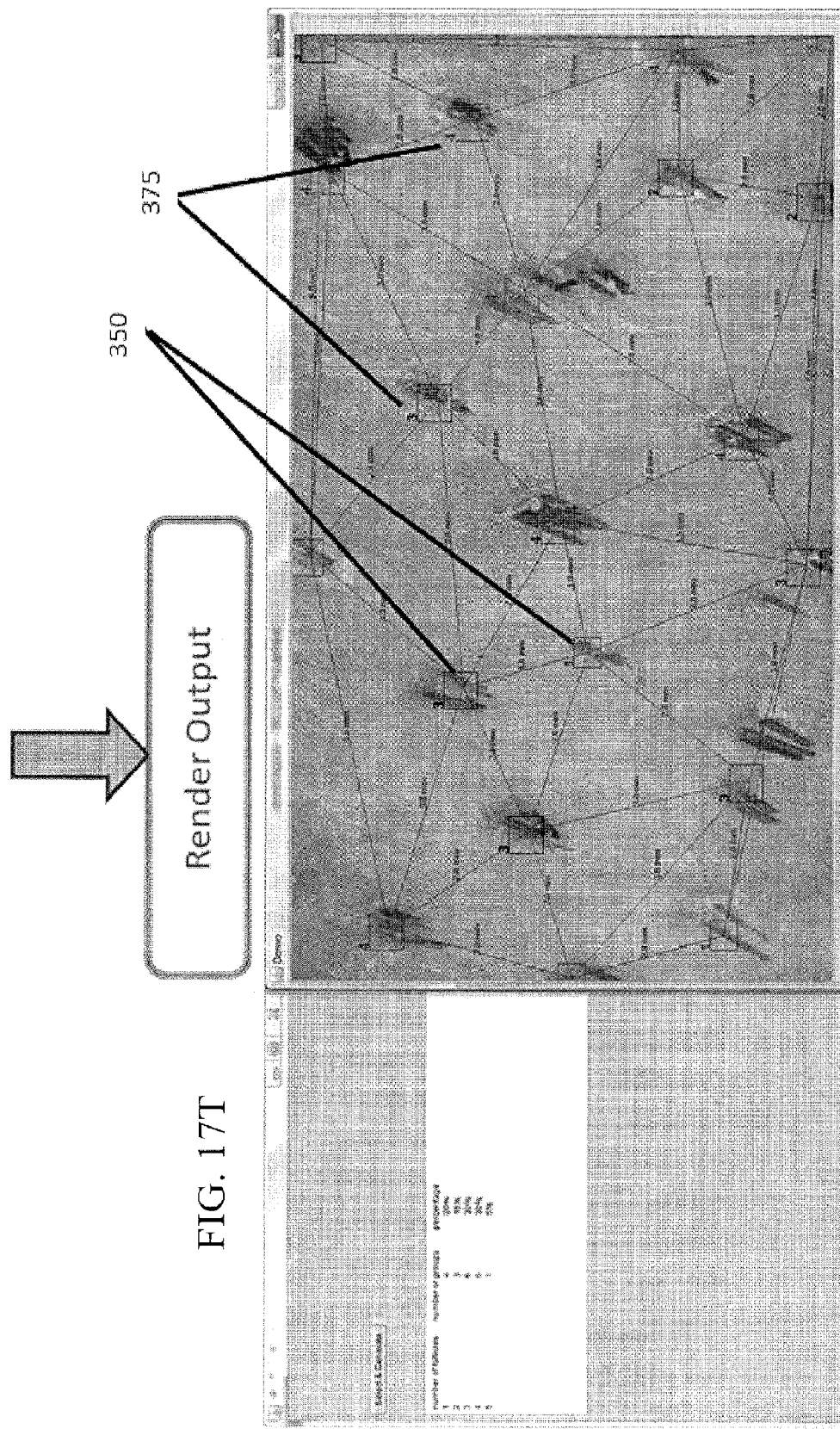

A mobile application was developed to utilize the systems and methods of the subject invention from any location. The mobile application can take the sample digital image and send it to a web server, through the world wide web, where a web service can receive the digital image. The web server can have installed thereon an embodiment of the algorithm of the subject invention and can process the image using the installed algorithm. After processing, the web server can provide the coordinates of one or more markers 350 along with one or more labels 375 that are also generated during analysis of the digital image. In one embodiment, a marker is a visual indicator of the location for each pixel cluster that represents a follicle group. In a further embodiment, each label is a number or other symbol in close proximity to the marker that it represents how many follicles are present at each marker position. The mobile application can obtain the marker and label information and display it on the digital image for final output to a user. FIG. 17T illustrates one example of this embodiment. Advantageously, this application can provide a framework for analysis of follicle images that physicians can utilize from their mobile devices, thus removing reliance on desktop computers. Also provided is an expert system to aid in the analysis and advice on the selection of medical procedure. Other mobile applications can be developed by providing a generic mobile application development framework that allows for access of other applications into the mobile domain.

One embodiment utilizes software which is capable of taking an image of a portion of a patients scalp and identify folical location and density. This information can be conveyed back to a user in the form of a report 500, illustrated, for example, in FIG. 17U, which can be used to plan a folical hair transplant. This information can easily be formatted and transmitted via a system interface for use by a robotic implantation system.

In a further embodiment, a physician utilizes a mobile device, such as, for example, a tablet or smart phone device, to acquire an image from a patient's scalp in the physicians office. The software can transmit the image to a web-based or cloud server where it will be analyzed and a Follicle Analysis report 500 sent back to the tablet or smart phone device with the necessary metrics provided to the physician. The results can be shared with the patient in near realtime so that the consultation can conclude in the patient being informed whether the technique can be used and what the expected results will look like.

In advance of a surgery, a robotic implantation device can receive the follicle pattern information from the here described system and use it to plan an implantation pattern based on the location of the baldness being treated. The industry is moving toward the use of assistive robotic systems that remove and implant patient hair follicles. Embodiments of the subject invention can be used to direct the operations of a robotic hair implant system to reduce the amount of time the surgeon must operate on the patient and can potentially reduce surgery costs for patients over time. Embodiments of the subject invention provide advantages that are currently not available in any robotic system, which is the ability to systematically identify the unique hair follicle patterns of a patient and render this information via a simple application programming interface (API). The API will allow a robotic system to acquire follicle placement information necessary to plan its objective area. In an embodiment, the robotic system will connect to a cloud-based service via an API and can transmit images from the patient's scalp, taken in the physician's office. Cloud servers having installed therein embodiments of the algorithm of the subject invention, can be used to analyze the image and send a report back to the robotic system via the API with the necessary metrics requested by the physician via the robotic system. The results can be shared with the patient in near realtime so that the consultation can conclude in the patient being informed whether this technique can be used and what the expected results will look like. With the planning data computed, the patient can return to the office for the procedure and the system can be initiated with the planned treatment.

A further advantage to the method of the subject invention is that it can enables a new grafting technique for implantation and this would help doctors to derive the distribution of hair follicles on the scalp in addition to their inter follicular distances. A graft can be produced to match original hair patterns exactly so that the implantation appears more natural.

Certain modifications of the imaged patterns should be incorporated in specific areas of the hair transplant to achieve optimal outcomes.

1) Frontal hairline: The leading edge of the hairline zone must be completely irregular and have no straight-line characteristics. The most peripheral areas of the hairline zone are grafted at a lower density and the density increases as one progresses inward. Exclusively single hair follicular units (preferably with finer caliber hairs) are utilized in the first 3 to 5 mm. wide area of the hairline zone. Occasionally some two hairs follicular units can be used interspersed within the single hairs towards the most posterior aspect of this zone. Behind the area just described the pattern can begin.

2) The "whorl" part of the posterior scalp or crown is an area that in common language is called the "cow lick area and measures approx. 1-2 cm in diameter. Hairs in this area are lie a vortex-type pattern radiating outwards in a 360° range of directions. Towards the center of the whorl mostly single hair follicular units are utilized with perhaps a rare two hair follicular unit interspersed. No three hair follicular units should be utilized in this area and it should be grafted at slightly lower density than the rest of the crown.

3) The "back hairline": When the front half to two thirds of the balding scalp is transplanted, the most posterior border of the transplanted zone is sometime referred to as the "back hairline". This area is composed of a zone approximately 2 to 3 cm wide in the anterior-posterior plane and should be characterized by total irregularity it and is never a straight line). In this "back hairline" the density is lower and is density gradually decreased as one goes more posteriorly. Predominantly one hair follicular units are utilized interspersed with some two hair follicular units. No three hair follicular units are used in this zone.

4) Temporal points—these are hair-bearing "peaks" similar in shape to a triangle with the apex pointing towards the front. The temporal points are located above the sideburns.

One-hair follicular units with low caliber hairs are used for 5 mm around the periphery with two-hair units used centrally. Lower densities are utilized to recreate these structures.

5) In most cases of advanced baldness, donor follicle limitations are such that transplantation can cover from the frontal hairline posteriorly to where the scalp starts transitioning from the horizontal to the vertical plane. This transition point has been termed the "vertex transition point". By transplanting up to this point, the changing scalp curvature is taken advantage of, as the transplanted hairs in this area fall and covers the vertical component of the crown. Since the crown can expand centrifugally with continuing baldness, it is best to not commit to transplantation of the vertical crown so that if hair loss continues inferiorly, one does not have to utilize precious donor supply to keep chasing the baldness in a downward direction.

The scope of the invention is not limited by the specific examples and suggested procedures and uses related herein since modifications can be made within such scope from the information provided by this specification to those skilled in the art.

Following examples illustrates procedures for practicing the subject invention. This example is provided for the purpose of illustration only and should not be construed as limiting. Thus, any and all variations that become evident as a result of the teachings herein or from the following examples are contemplated to be within the scope of the present invention.

Example 1

Experimental Results

Figure 12:
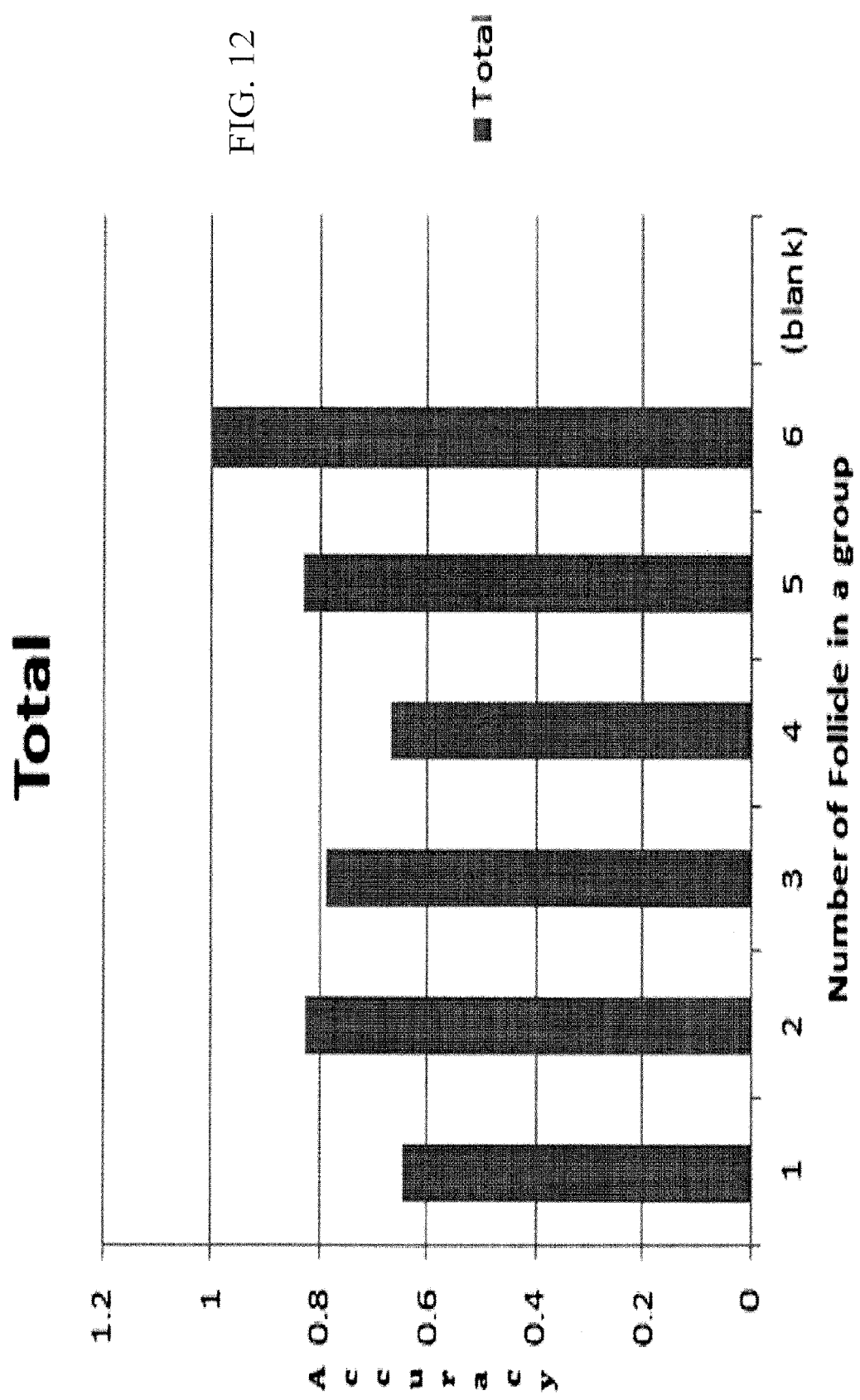
FIG. 12 is a graph showing the average accuracy of the embodiments of the subject invention.

The methods of the subject invention were conducted on several different types of sample images obtained from real patients. The results are shown in FIG. 16. The graph shown in FIG. 12 depicts average accuracy for each follicle groups.
Follicle Detection Accuracy Accuracy can be determined from two dimensions: a) how many follicles are undetected, and b) how many counts of follicle are incorrect. The methods of the subject invention provide results that are accurate in terms of detecting the follicle instances. Almost no follicle particle is undetected. Then accuracy in terms of correct count of follicles can be calculated by the following formula, $$\text{accuracy} = \begin{cases} \frac{\text{actual}}{\text{detected}} \times 100 & \text{if detected} \geq \text{actual} \\ \frac{\text{detected}}{\text{actual}} \times 100 & \text{if actual} > \text{detected} \end{cases} \quad (9)$$

In one case, 5 groups of follicles was indicated where the number of follicles was actually 3. The methods and algorithms of the subject invention detected 6 such groups. So the accuracy was determined to be ⅚=83.33%. As seen in FIG. 16, most of the time, accuracy was over 80%, which is quite good for these types of noisy, blurry, nonstandard image samples. The methods herein could identify all the follicle groups successfully. Interestingly, the total number of actual follicles is usually greater than the number of follicles detected by our system. This is due to the subtraction of some border regions early in the method to reduce noise, which can eliminate some follicles.

The methodology worked well on almost all of the sample images regardless of the size of the follicles and level of image noise. For example, the input images seen in FIG. 13 and FIG. 14 have a lot of differences between them. FIG. 13 is a clearer image, but the follicles are not dark enough. FIG. 14 is very noisy, but the follicles are dark enough to see. FIG. 15 illustrates results obtained from an image with less initial noise. The methods and algorithms of the subject invention were able to accurately detect follicle groups for both of the images. This is due to the application of thresh holding to separate the follicles from background and reduction of other noise by applying Gaussian Blur and gray imaging techniques. Advantageously, grayscale imaging gives dark follicles regardless of the original color of follicles. Finally in the counting phase, merging the follicle pixels ensures that there will not be much difference between long and short follicles in the number of follicle pixel groups.

CONCLUSION

The methods of the subject invention provide a generalized way to count any type of shape or region of interest within an image. Currently existing standard methods can work on specific images with specific shapes. But they usually have so many constraints on the quality of the input image that they can be impractical to use. The subject invention applies simple techniques to detect the corners of a quadrilateral object, detecting and merging the connected pixels to form follicle particles, and finally a recursive clustering algorithm to cluster them. Results were found to be acceptably accurate in terms of object (follicle) count. The method can be applied not only follicle detection, but any type of noisy or heavily cluttered images, especially medical or biological images where the randomly scattered objects need to be detected and counted. FIG. 17A to FIG. 17U provide a graphical illustration of one embodiment for practicing the methods and procedures of the subject invention. In a particular embodiment, a Follicle Analysis Report 500 is generated, such as shown, for example, in FIG. 17U. The report provides metrics that can be used to determine whether a patient is a viable candidate for the procedures.

This system for clustering hair follicle units is unique because it groups the individual follicles, which reside very close together on the human scalp, and computes a percentage for each on the basis of whether it contains 1, 2, 3 or 4 follicle(s) per cluster. This, in turn, can be used to obtain the patient's hair follicle density. The technique can further merge follicular units which are then inputted into a clustering algorithm in order to group the follicle pixels together. The results are then used in an approximation model to map the number of merged follicle pixels to the number of follicles per cluster. The more follicle pixels detected in a cluster, the more follicles that reside within the cluster. The system used in claim one, comprises acquisition components, which use mobile phones and microscopes to capture the input images.

The technology is based on an algorithm that uses a unique context dependent framework wherein directional progression of pixels, which is part of a follicle, is used to merge the follicle pixels for identifying follicle units. Specifically, directional progression is used to measure the angle of a follicle on the vertical axis. This allows the physician to know in which direction the patient's hair grows. Furthermore, the angle of growth for each follicle can help the physician know, using the sample image, which part of the scalp it was taken from. For example, the sample taken from the crown area of the scalp has different angles of growth compared to the back of the skull.

Input images can be sent to a hybrid cloud for analysis where the image processing software kernel resides. This introduces the application in the context of telemedicine for hair implantation. In addition, a centralized client server system can been incorporated. The hair implantation robots can be the clients and will be connected to a central cloud server. All the robots can have extensive processing power and their software will be updated regularly through the parent server.

Finally, the system enables the computation of the inner follicular distances using a graph model to connect neighboring follicular units by calculating the distance between each edge. There are no edge crossings to obtain a standard connected sample. Furthermore, a hair follicle mosaic model generated is the patient's signature, which can be used to identify the user. This would also enable recognition of the nationality of a person from this signature. For example, driven profiling of patients from Latin America (mostly mixed complexion) differ greatly, in terms of hair signature, when compared to patients from North America (mostly white complexion).

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and that various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

REFERENCES

[1] Shehrzad A. Qureshi, Mohan Bodduluri, System and method for counting follicular units, U.S. Pat. No. 8,290, 229 B2, U.S. application Ser. No. 13/472,631, Restoration Robotics, Inc, 2012

[2] Hoffmann and Rolf, TrichoScan: a novel tool for the analysis of hair growth in vivo, Journal of Investigative Dermatology Symposium Proceedings, volume 8, pages 109-115, 2003. web link http://www.ncbi.nlm.nih.gov/pmc/articles/PMC3002414/.

[3] Victor Lempitsky, Andrew Zisserman, Learning To Count Objects in Images, NIPS, 2010.

[4] Thomas Kalinke, Christos Tzomakas, and Werner v. Seelen, A Texture based Object Detection and an adaptive Model-based Classification, IEEE International Conference on Intelligent Vehicles, 1998.

[5] D. Girish Kumar, M. Padmaja, A novel image processing technique for counting the number of trees in a satellite image, European Journal of Applied Engineering and Scientific Research, 2012, 1 (4):151-159.

We claim:

1. A method for extracting information of interest from an image and counting occurrences of the information of interest within the image, the method comprising:
   a. obtaining a digital image,
   b. normalizing a region of interest to obtain an area for analysis,
   c. enhancing information of interest in the area for analysis by removing undesired information,
   d. analyzing each pixel within the enhanced information of interest in the digital image to determine those pixels within a particular color range,
   e. recording a position for each pixel within the particular color range,
   f. creating a number of clustered pixels by clustering the pixels within the particular color range based upon the recorded position of each pixel,
   g. determining a number of occurrences of information of interest by the number of clustered pixels,
   h. determining distances between clustered pixels, and
   i. creating a graph of connected vertices on the image, wherein the vertices do not cross.

2. The method of claim 1, wherein enhancing information of interest comprises increasing the contrast between pixels within the digital image.

3. The method of claim 1 wherein normalizing the region of interest comprises extracting a quadrilateral area from the digital image, comprising the steps of:
   a. detecting at least two corners of the region of interest and at least two corners of the digital image,
   b. making a virtual connection between the corners of the region of interest and the corners of the digital image,
   c. rotating the digital image until the length of the virtual connections between the corners are minimized, and
   d. cropping the region of interest from the digital image.

4. The method of claim 1, further comprising providing a report that includes at least one metric regarding the region of interest.

5. The method of claim 4, wherein the at least one metric is the number of occurrences of the information of interest within the image area.

6. The method of claim 5, wherein at least one metric is the distance between occurrences of the information of interest within the image area.

7. The method of claim 6, wherein the metrics are utilized in hair transplant surgery.

8. The method of claim 7, wherein the metrics are formatted for use in a robotic hair implantation system.

9. A system for directing a follicle implantation procedure, the system comprising:

a mobile device having stored thereon computer-usable instructions, where the mobile device is utilized to obtain a digital image of a region of interest for implantation;

a computer readable medium having stored thereon an algorithm that, when implemented,
a. receives the digital image from the mobile device,
b. normalizes the region of interest in the digital image to obtain an area for analysis,
c. enhances information of interest in the area for analysis by removing undesired information,
d. analyzes each pixel within the area for analysis to determine those within a particular color range,
e. records a position for each pixel within the particular color range,
f. clusters the pixels within the particular color range based upon the recorded position of each pixel, and
g. determines a number of follicle occurrences by utilizing the clustered pixels,
h. generates at least one marker indicating a position for each follicle occurrence,
i. generates at least one label for each marker that indicates a number of follicle groups within the marker, and
j. transmits the at least one marker and the at least one label to the mobile device, such that the one or more markers and the one or more labels are used to generate a follicle implantation pattern for use during the follicle implantation procedure.

10. The system, according to claim 9, wherein the one or more markers and the one or more labels is transmitted to the mobile device as a report.

11. The system, according to claim 10, further comprising:
a robotic implantation device that receives the report from the mobile device, where the robotic implantation device utilizes the report to generate the follicle implantation pattern for use during the follicle implantation procedure.

12. The system, according to claim 10, further comprising transmitting the at least one marker and the at least one label as a report to a robotic implantation device that utilizes the report to generate the follicle implantation pattern for use during the follicle implantation procedure.

13. The system, according to claim 10, wherein the computer readable medium on which the algorithm is stored is accessible by the mobile device through the world wide web.

14. The system, according to claim 9, further comprising
a. determining the distances between clustered pixels,
b. creating a graph of connected vertices between the clustered pixels on the digital image, and
c. transmitting the graph as part of the report to the mobile device in a format viewable on the mobile device.

15. The system, according to claim 9, wherein to normalize the region of interest comprises extracting a quadrilateral area from the digital image, comprising the steps of:
a. detecting at least two corners of the region of interest and at least two corners of the digital image,
b. making a virtual connection between the corners of the region of interest and the corners of the digital image,
c. rotating the digital image until the length of the virtual connections between the corners are minimized, and
d. cropping the region of interest from the digital image.

16. A method for conducting a hair follicle implantation procedure comprising:
obtaining a digital image of a region of interest for implantation;
transmitting the digital image of the region of interest to a computer with a computer readable medium having stored thereon an algorithm that, when implemented,
a. normalizes the region of interest in the digital image to obtain an area for analysis,
b. enhances information of interest in the area for analysis by removing undesired information,
c. analyzes each pixel within the area for analysis to determine those within a particular color range,
d. records a position for each pixel within the particular color range,
e. clusters the pixels within the particular color range based upon the recorded position of each pixel,
f. determines a number of follicle occurrences by utilizing the clustered pixels,
g. generates at least one marker indicating a position for each follicle occurrence, and
h. generates at least one label for each marker that indicates a number of follicle groups within the marker,
such that the one or more markers and the one or more labels are used to generate a follicle implantation pattern for use during the follicle implantation procedure.

17. The method, according to claim 16, wherein the digital image is obtained with a mobile device that transmits the digital image to the computer.

18. The method, according to claim 17, further comprising transmitting the at least one marker and the at least one label as a report to a robotic implantation device, where the robotic implantation device utilizes the report to generate a follicle implantation pattern for use during the follicle implantation procedure.

19. The method, according to claim 16, wherein to normalize the region of interest comprises extracting a quadrilateral area from the digital image, comprising the steps of:
a. detecting at least two corners of the region of interest and at least two corners of the digital image,
b. making a virtual connection between the corners of the region of interest and the corners of the digital image,
c. rotating the digital image until the length of the virtual connections between the corners are minimized, and
d. cropping the region of interest from the digital image.

20. The method of claim 2, wherein analyzing each pixel comprises examining at least one other pixel in contact with the pixel being analyzed.

* * * * *